United States Patent [19]

Amishiro et al.

[11] Patent Number: 5,641,780
[45] Date of Patent: Jun. 24, 1997

[54] PYRROLO-INDOLE DERIVATIVES

[75] Inventors: Nobuyoshi Amishiro, Shizuoka; Satoru Nagamura, Hofu; Hiromitsu Saito, Kawasaki; Eiji Kobayashi, Tokyo; Akihiko Okamoto, Numazu; Katsushige Gomi, Susono, all of Japan

[73] Assignee: Kyowa Hakko Kogyo Co., Ltd., Tokyo, Japan

[21] Appl. No.: 564,178

[22] PCT Filed: Apr. 20, 1995

[86] PCT No.: PCT/JP95/00779

§ 371 Date: Dec. 15, 1995

§ 102(e) Date: Dec. 15, 1995

[87] PCT Pub. No.: WO95/29179

PCT Pub. Date: Nov. 2, 1995

[30] Foreign Application Priority Data

Apr. 22, 1994 [JP] Japan .................... 6-084714

[51] Int. Cl.$^6$ .................... A61K 31/495; C07D 487/04
[52] U.S. Cl. .................... 514/253; 544/142; 544/373; 546/187; 548/433
[58] Field of Search .................... 544/142, 373; 546/187; 548/433; 514/253, 232.8, 216, 411

[56] References Cited

U.S. PATENT DOCUMENTS 5,070,092 12/1991 Kanda et al. .................... 544/373
5,258,383 11/1993 Nagamura et al. .................... 544/373

FOREIGN PATENT DOCUMENTS 154445 2/1985 European Pat. Off. .
502005 7/1990 Japan .

Primary Examiner—Mukund J. Shah
Assistant Examiner—Pavanaram K. Sripada
Attorney, Agent, or Firm—Fitzpatrick, Cella, Harper & Scinto

[57] ABSTRACT

DC-89 derivatives represented by the formula

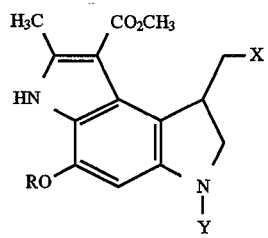

wherein X represents CL or Br; R represents substituted or unsubstituted alkyl, substituted or unsubstituted aralkyl, $COR^1$ or $S_2OR^7$; and Y represents

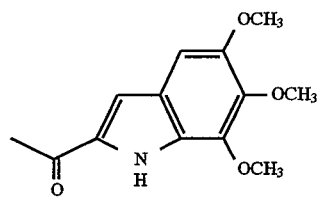

or

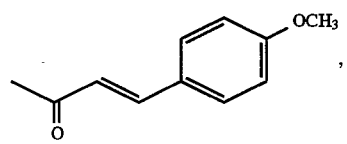

and pharmaceutically acceptable salts thereof.

The compounds of the present invention exhibit excellent anti-tumor activity and are useful as anti-tumor agents.

3 Claims, No Drawings 5,641,780

1

PYRROLO-INDOLE DERIVATIVES

This application is a 371 of PCT/JP95/00779 Apr. 20, 1995.

TECHNICAL FIELD

The present invention relates to DC-89 derivatives. The compounds of the present invention exhibit excellent anti-tumor activity and are useful as anti-tumor agents.

BACKGROUND ART

As compounds related to DC-89 derivatives of the present invention, DC-89A1, DC-89A2, DC-89B1 and DC-89B2 represented by the following structural formula are known, and these compounds exhibit antibacterial activity against various bacteria and also antitumor activity against melanoma B-16, etc.

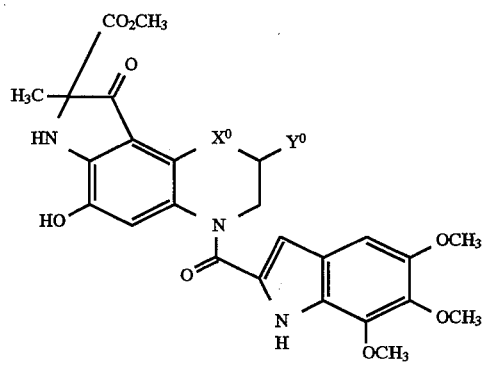

2

DC-89A1 : $X^0$=—$CH_2$—, $Y^0$=Cl

DC-89A2: $X^0$=single bond, $Y^0$=$CH_2Cl$

DC-89B1 : $X^0$=—$CH_2$—, $Y^0$=Br

DC-89B2: $X^0$=single bond, $Y^0$=$CH_2Br$

DC-89A1 is disclosed in WO87/06265, and DC-89A2, DC-89B1 and DC-89B2 are disclosed in JP,A,2-119787. SF2582A and SF2582B, which are the same compounds as DC-89A2 and DC-89A1, are disclosed in JP,A,1-139590. DC-88A and DC113 are disclosed in WO87/06265 and JP,A,2-177890, respectively. These compounds exhibit not only antibacterial activity against various bacteria but also anti-tumor activity against melanoma B-16, etc.

DC-88A derivatives and DC-89 derivatives are disclosed in JP,A,2-288879, JP,A,3-7287, JP,A,3-128379 and JP,A,5-178858.

JP,A,3-128379 discloses Compounds (A) and (C) represented by the following formulae, and JP,A,5-178858 discloses Compounds (B) and (D) represented by the following formulae.

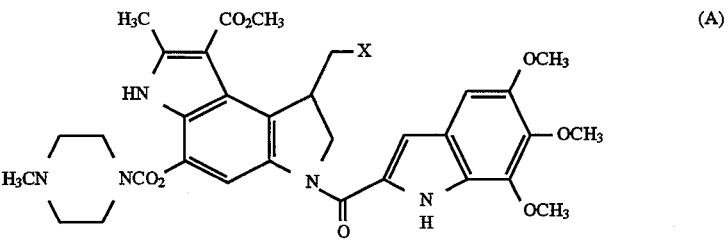
(A)

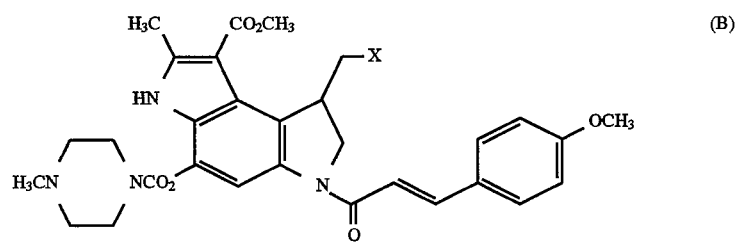
(B)

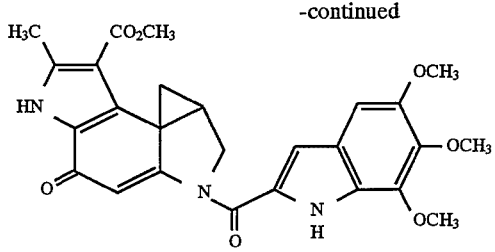

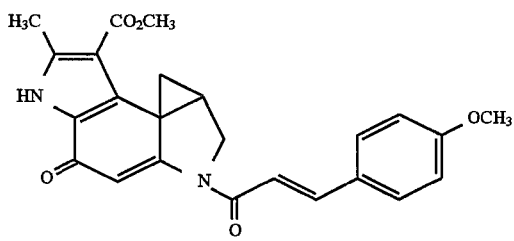

Further, CC-1065 and its derivatives are disclosed in JP,A,54-64695, JP,A,60-193989, WO88/04659, EP-359454 and JP,A,3-14581. Related derivatives are disclosed in JP,A, 6-116269.

It is an object of the present invention to provide DC-89 derivatives which exhibit excellent anti-tumor activity.

DISCLOSURE OF THE INVENTION

The present invention provides DC-89 derivatives represented by formula (I)

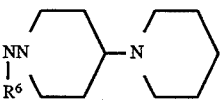

(I)

wherein X represents Cl or Br; R represents substituted or unsubstituted lower alkyl, substituted or unsubstituted aralkyl, $COR^1$ {in which $R^1$ represents hydrogen, substituted or unsubstituted lower alkyl, substituted or unsubstituted aryl, substituted or unsubstituted heterocyclic group, $OR^2$ (in which $R^2$ represents substituted or unsubstituted lower alkyl or aryl), $SR^2$ (in which $R^2$ is the same meaning as defined above), $NR^3R^4$ (in which $R^3$ and $R^4$ independently represent hydrogen, substituted lower alkyl, amino, or mono- or di(lower alkyl)amino, provided that $R^3$ and $R^4$ are not hydrogen at the same time),

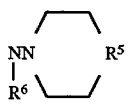

in which $R^5$ represents $NR^7$ (in which $R^7$ represents hydrogen or substituted or unsubstituted lower alkyl) or oxygen, and $R^6$ is the same meaning as $R^7$ defined above or

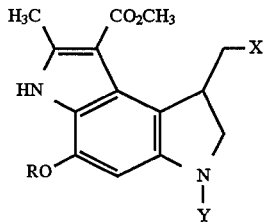

(in which $R^6$ is the same meaning as defined above)} or $SO_2R^8$ (in which $R^8$ represents substituted or unsubstituted lower alkyl or substituted or unsubstituted aryl); and Y represents

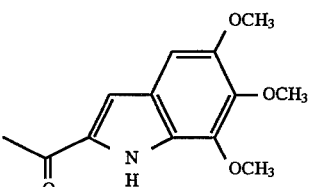

or

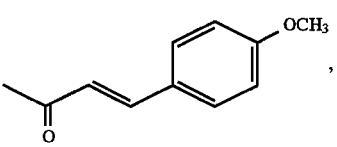

and pharmaceutically acceptable salts thereof.

The compounds represented by formula (I) are hereinafter referred to as Compounds (I). Similarly, the compounds represented by formulae (I) to (IX) are referred to as Compounds (I) to (IX). Compounds (I)a, (I)b, etc. are intended to be included in Compounds (I), and Compounds (I)b-1, (I)b-2, etc. are intended to be included in Compounds (I)b.

In the definition of the above-mentioned formula (I), lower alkyl and the alkyl moiety of mono- or di(lower alkyl)amino include linear or branched alkyl groups having 1 to 8 carbon atoms such as methyl, ethyl, propyl, isopropyl, butyl, isobutyl, sec-butyl, tert-butyl, pentyl, isopentyl, hexyl, isohexyl, heptyl, octyl and iso-octyl. Examples of aryl include phenyl and naphthyl. Examples of aralkyl include groups having 7 to 20 carbon atoms such as benzyl, phenetyl, styryl, benzhydryl and trityl. Examples of the heterocyclic group include pyridyl, pyrazinyl and pyrimidinyl. The substituted lower alkyl has 1 to 3 independently-selected substituents such as lower alkoxy, alkylthio optionally substituted by carboxy, carboxy, lower alkoxycarbonyl, benzyloxycarbonyl, amino, mono- or di(lower alkyl)amino, cyclic amino optionally substituted by lower alkyl or cyclic amino, halogen and phenyl, in which examples of the cyclic amino group include pyrrolidino, piperidino, piperazinyl and morpholino, and lower alkyl and the alkyl moiety of lower alkoxy, lower alkylthio, lower alkoxycarbonyl and mono- or di(lower alkyl)amino has the same definition as that of the above-mentioned lower alkyl. Examples of halogen include fluorine, chlorine, bromine and iodine atoms. The substituted aryl, the substituted aralkyl and the substituted heterocyclic group each has 1 to 3 independently-selected substituents such as lower alkyl, substituted alkyl, lower alkoxy, lower alkoxycarbonyl, amino, mono- or di(lower alkyl)amino, pyrrole and halogen, in which lower alkyl and the alkyl moiety of lower alkoxycarbonyl and mono- or di(lower alkyl)amino has the same definition as that of the above-mentioned lower alkyl, and the substituents of substituted lower alkyl and halogen are the same meanings as defined above.

Examples of the pharmaceutically acceptable salts of Compounds (I) include inorganic acid-addition salts such as hydrochloride, hydrobromide, hydroiodide, sulfate, phosphate and nitrate, and organic acid-addition salts such as acetate, benzoate, maleate, fumarate, succinate, tartrate, citrate, oxalate, glyoxylate, aspartate and methanesulfonate.

The processes for preparing Compounds (I) are described below.

When the defined groups changes under reaction conditions or are inappropriate for conducting the processes, the processes can be easily carried out by using protection/deprotection method for functional groups conventionally employed in organic synthetic chemistry including oxidation, reduction and hydrolysis.

Process 1

Compound (I)a, which is Compound (I) wherein R is substituted or unsubstituted lower alkyl or substituted or unsubstituted aralkyl, can be prepared by the following process.

Process 1-1

Compound (II) can be prepared by treating Compound (C) or Compound (D) with perchloric acid in an inert solvent.

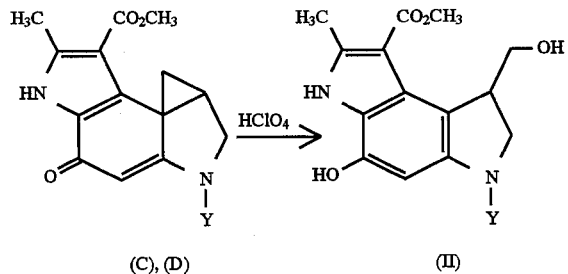

In the formulae, Y is the same meaning as defined above.

Perchloric acid is usually used in an amount of 1 to 20 equivalents based on Compound (C) or (D).

As the inert solvent, water, dimethylformamide, tetrahydrofuran, toluene, dioxane, acetonitrile, etc. may be used singly or in combination. The reaction is usually conducted at −20° C. to 50° C. for 10 minutes to 10 hours.

Process 1-2

Compound (IV) can be prepared by reacting Compound (II), in the presence of a base in an inert solvent, with R⁹—Hal (III)

wherein R⁹ is substituted or unsubstituted lower alkyl or substituted or unsubstituted aralkyl in the definition of R, and Hal is a chlorine, bromine or iodine atom.

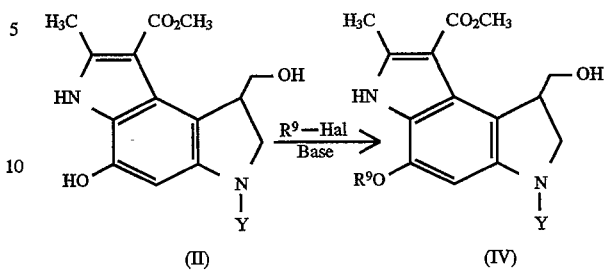

In the formulae, R⁹ and Y are the same meanings as defined above.

Compound (III) is usually used in an amount of 1 to 10 equivalents based on Compound (II). Examples of the base include potassium carbonate, sodium hydrogen carbonate, potassium tert-butoxide, triethylamine, pyridine and 4-dimethylaminopyridine. The base is usually used in an amount of 1 to 10 equivalents based on Compound (II). As the inert solvent, dimethylformamide, acetone, tetrahydrofuran, toluene, dioxane, acetonitrile, etc. may be used singly or in combination. The reaction is usually conducted at −20° C. to 80° C. for 1 hour to 3 days.

Process 1-3

Compound (V) can be prepared by reacting Compound (IV) with methanesulfonyl chloride in the presence of a base in an inert solvent.

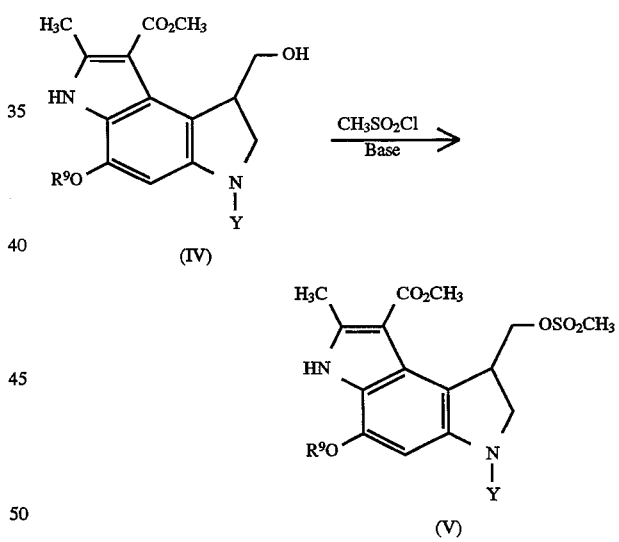

In the formulae, R⁹ and Y are the same meanings as defined above.

Methanesulfonyl chloride is usually used in an amount of 1 to 5 equivalents based on Compound (IV). Examples of the base include potassium tert-butoxide, triethylamine, pyridine and 4-dimethylaminopyridine. The base is usually used in an amount of 1 to 5 equivalents based on Compound (IV). However, when the base serves also as a solvent, it is used in large excess. As the inert solvent, pyridine, methylene chloride, chloroform, dimethylformamide, tetrahydrofuran, toluene, dioxane, etc. may be used singly or in combination. The reaction is usually conducted at −80° C. to 50° C. for 30 minutes to 1 day.

Process 1-4

Compound (I)a can be prepared by reacting Compound (V), in an inert solvent, with Met—X  (VI)

wherein Met is an alkali metal such as lithium, sodium and potassium, and X is the same meaning as defined above.

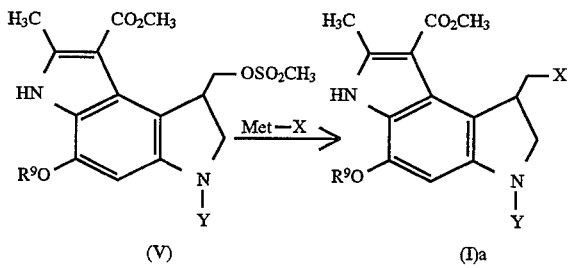

In the formulae, $R^9$, Met, X and Y are the same meanings as defined above.

Compound (VI) is usually used in an amount of 1 to 20 equivalents based on Compound (V). As the inert solvent, dimethylformamide, dimethylsulfoxide, tetrahydrofuran, toluene, dioxane, acetonitrile, etc. may be used singly or in combination. The reaction is usually conducted at 0° C. to 100° C. for 30 minutes to 2 days.

Process 2

Compound (I)b, which is Compound (I) wherein R is $COR^1$ in which $R^1$ is the same meaning as defined above, can be prepared by the following process.

Process 2-1

Compound (VII) can be prepared by treating Compound (C) or Compound (D) with hydrochloric acid or hydrobromic acid in an inert solvent.

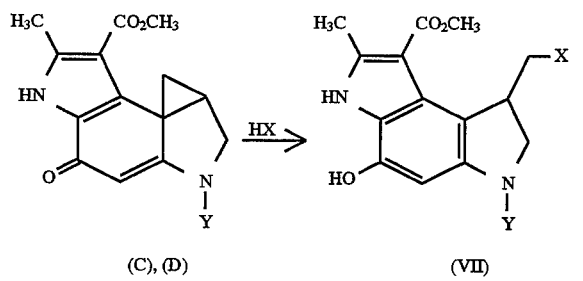

In the formulae, X and Y are the same meanings as defined above.

Hydrochloric acid or hydrobromic acid is usually used in an amount of 1 to 20 equivalents based on Compound (C) or (D). As the inert solvent, water, dimethylformamide, tetrahydrofuran, dioxane, acetonitrile, etc. may be used singly or in combination. The reaction is usually conducted at −30° C. to 50° C. for 10 minutes to 5 hours.

Compound (C) can be prepared from Compound (E) having the following structure, which is a precursor of Compound (C), by the process desclosed in JP,A,3-128379. Compound (C) thus obtained also may be used without isolation in the above process.

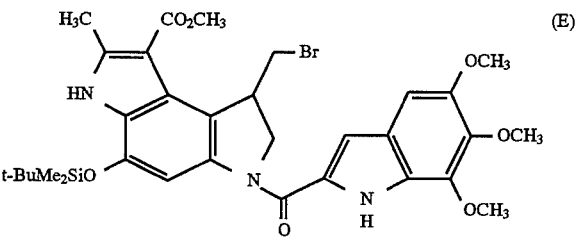

In the formula, Me represents a methyl group, and t—Bu represents a tert-butyl group.

Process 2-2-1

Compound (I)b-1, which is Compound (I)b wherein $R^1$ is hydrogen, substituted or unsubstituted alkyl, substituted or unsubstituted aryl or substituted or unsubstituted heterocyclic group, can be prepared by reacting Compound (VII), in an inert solvent, with a condensation agent such as dicyclohexylcarbodiimide (DCC), 4-dimethylaminopyridine and $R^{10}CO_2H$ (in which $R^{10}$ is hydrogen, substituted or unsubstituted alkyl, substituted or unsubstituted aryl or substituted or unsubstituted heterocyclic group in the definition of $R^1$).

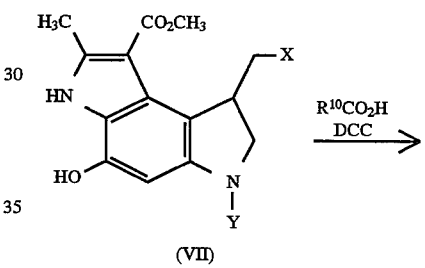

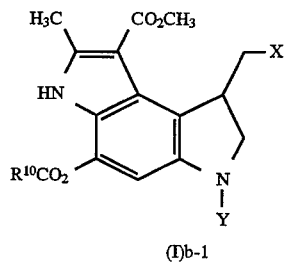

In the formulae, $R^{10}$, X and Y are the same meanings as defined above.

$R^{10}CO_2H$, DCC and 4-dimethylaminopyridine are usually used in amounts of 1 to 10 equivalents based on Compound (VII). As the inert solvent, methylene chloride, chloroform, dimethylformamide, tetrahydrofuran, toluene, dioxane, acetonitrile, etc. may be used singly or in combination. The reaction is usually conducted at −20° C. to 50° C. for 1 hour to 1 day.

Process 2-2-2

Compound (I)b-1 can be prepared by reacting Compound (VII) with an acid anhydride represented by the formula $(R^{10}CO)_2O$ in which $R^{10}$ is the same meaning as defined above in the presence of a base in an inert solvent.

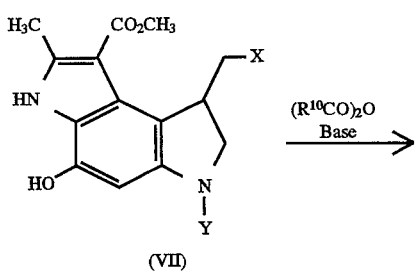

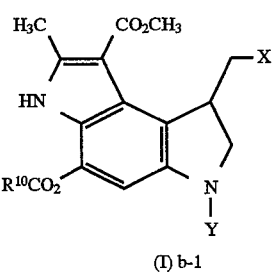

(I)b-1

In the formulae, $R^{10}$, X and Y are the same meanings as defined above.

The acid anhydride is usually used in an amount of 1 to 10 equivalents based on Compound (VII). Examples of the base include triethylamine, pyridine and 4-dimethylaminopyridine. The base is usually used in an amount of 1 to 10 equivalents based on Compound (VII). However, when the base serves also as a solvent, it is used in large excess. As the inert solvent, methylene chloride, chloroform, dimethylformamide, tetrahydrofuran, toluene, dioxane, pyridine, etc. may be used singly or in combination. The reaction is usually conducted at −20° C. to 50° C. for 30 minutes to 1 day.

Process 2-3

Compound (I)b-2, which is Compound (I)b wherein $R^1$ is $OR^2$ or $SR^2$ in which $R^2$ is the same meaning as defined above, can be prepared by reacting Compound (VII) with $$R^2\text{—Z—COCl} \quad \text{(VIII)}$$

wherein Z is oxygen or sulfur, and $R^2$ is the same meaning as defined above in the presence of a base in an inert solvent.

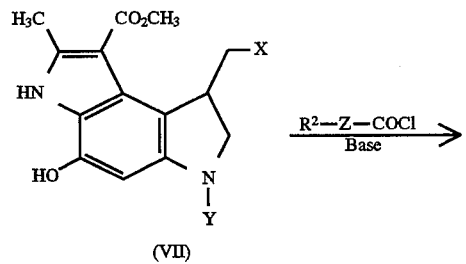

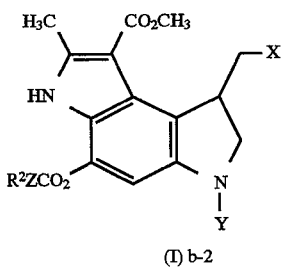

(I) b-2

In the formulae, X, Y, Z and $R^2$ are the same meanings as defined above.

Compound (VIII) is usually used in an amount of 1 to 10 equivalents based on Compound (VII). Examples of the base include potassium tert-butoxide, triethylamine, pyridine and 4-dimethylaminopyridine. The base is usually used in an amount of 1 to 10 equivalents based on Compound (VII). However, when the base serves also as a solvent, it is used in large excess. As the inert solvent, methylene chloride, chloroform, dimethylformamide, tetrahydrofuran, toluene, dioxane, pyridine, etc. may be used singly or in combination. The reaction is usually conducted at −80° C. to 50° C. for 30 minutes to 1 day.

Process 2-4

Compound (I)b-3, which is Compound (I)b wherein $R^1$ is $NR^{3a}R^{4a}$ wherein $R^{3a}$ and $R^{4a}$ independently represent hydrogen or substituted or unsubstituted lower alkyl in the definition of $R^3$ and $R^4$, can be prepared by the following process.

Process 2-4-1

Compound (IX) can be prepared by reacting Compound (VII) with p-nitrophenyl chloroformate in the presence of a base in an inert solvent.

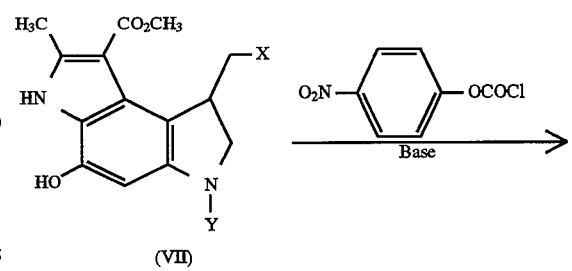

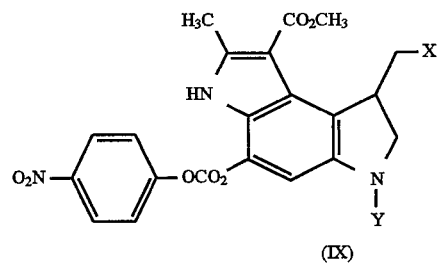

(IX)

In the formulae, X and Y are the same meanings as defined above.

p-Nitrophenyl chloroformate is usually used in an amount of 1 to 5 equivalents based on Compound (VII). Examples of the base include potassium tert-butoxide, triethylamine, pyridine and 4-dimethylaminopyridine. The base is usually used in an amount of 1 to 5 equivalents based on Compound (VII). However, when the base serves also as a solvent, it is used in large excess. As the inert solvent, methylene chloride, chloroform, pyridine, dimethylformamide, tetrahydrofuran, toluene, dioxane, etc. may be used singly or in combination. The reaction is usually conducted at −80° C. to 30° C. for 30 minutes to 10 hours.

Process 2-4-2

Compound (I)b-3 can be prepared by reacting Compound (IX) with $R^3R^4NH$ (in which $R^3$ and $R^4$ are the same meanings as defined above) in the presence of a base in an inert solvent.

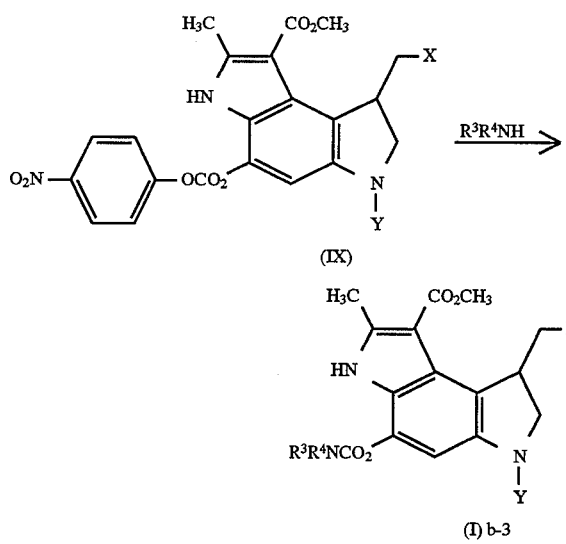

(IX)

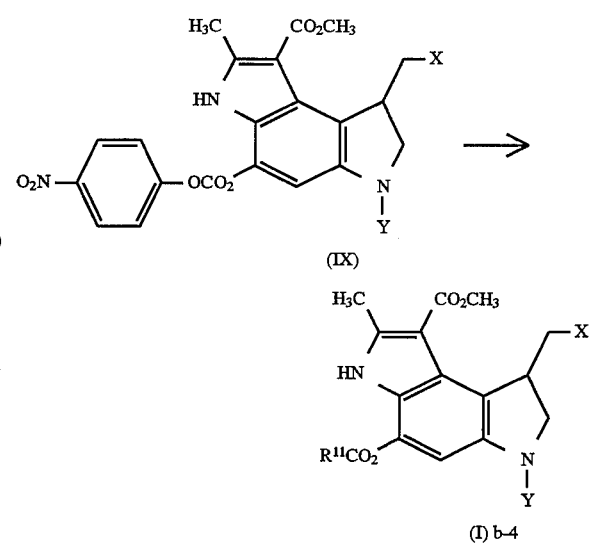

(IX)

(I)b-3

(I)b-4

In the formulae X, Y, $R^3$ and $R^4$ are the same meanings as defined above.

$R^3R^4NH$ is usually used in an amount of 1 to 5 equivalents based on Compound (IX). Examples of the base include triethylamine, pyridine and 4-dimethylaminopyridine. The base is usually used in an amount of 1 to 5 equivalents based on Compound (IX). However, when the base serves also as a solvent, it is used in large excess. As the inert solvent, methylene chloride, chloroform, dimethylformamide, tetrahydrofuran, toluene, dioxane, etc. may be used singly or in combination. The reaction is usually conducted at −80° C. to 80° C. for 30 minutes to 1 day.

Process 2-5

Compound (I)b-4, which is Compound (I)b wherein $R^1$ is $NR^{3b}R^{4b}$ (in which $R^{3b}$ and $R^{4b}$ independently represent hydrogen, amino or mono- or di(lower alkyl)amino in the definition of $R^3$ and $R^4$) or

(in which $R^5$ and $R^6$ are the same meanings as defined above), can be prepared by reacting Compound (IX), in the presence of a base in an inert solvent, with $HNR^{3b}R^{4b}$ (X) a or

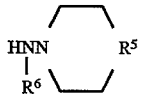 (X) b wherein $R^{3b}$, $R^{4b}$, $R^5$ and $R^6$ are the same meanings as defined above.

In the formulae, $R^{11}$ is $NR^{3b}R^{4b}$ (in which $R^{3b}$ and $R^{4b}$ are the same meanings as defined above) or

(in which $R^5$ and $R^6$ are the same meanings as defined above) in the definition of $R^1$, and X and Y are the same meanings as defined above.

Compound (X) is usually used in an amount of 1 to 5 equivalents based on Compound (IX). Examples of the base include triethylamine, pyridine and 4-dimethylaminopyridine. The base is usually used in an amount of 1 to 5 equivalents based on Compound (IX). However, when the base serves also as a solvent, it is used in large excess. As the inert solvent, methylene chloride, chloroform, dimethylformamide, tetrahydrofuran, toluene, dioxane, etc. may be used singly or in combination. The reaction is usually conducted at −80° C. to 50° C. for 30 minutes to 1 day.

Process 3

Compound (I)c, which is Compound (I) wherein R is $SO_2R^8$ (in which $R^8$ is the same meaning as defined above), can be prepared by reacting Compound (VII), in the presence of a base in an inert solvent, with Compound (XI) represented by the formula $R^8SO_2Cl$ (XI)

wherein $R^8$ is the same meaning as defined above.

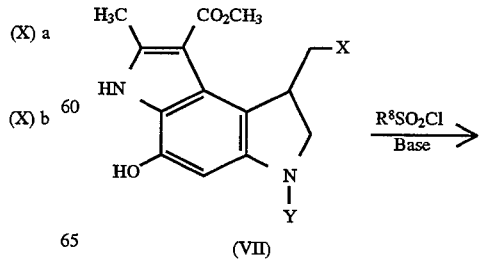

(VII)

-continued

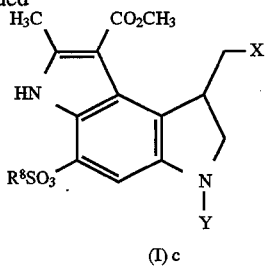

(I)c

In the formulae, $R^8$, X and Y are the same meanings as defined above.

Compound (XI) is usually used in an amount of 1 to 10 equivalents based on Compound (VII). Examples of the base include potassium tert-butoxide, triethylamine, pyridine and 4-dimethylaminopyridine. The base is usually used in an amount of 1 to 5 equivalents based on Compound (VII). However, when the base serves also as a solvent, it is used in large excess. As the inert solvent, methylene chloride, chloroform, dimethylformamide, pyridine, tetrahydrofuran, toluene, dioxane, etc. may be used singly or in combination. The reaction is usually conducted at −80° C. to 50° C. for 30 minutes to 20 hours.

After the completion of the reaction of each process, water, acid, buffer, an aqueous solution of sodium hydrogen carbonate, etc. are added to the reaction mixture, if necessary, and the mixture is extracted with an organic solvent such as ethyl acetate, chloroform and ether. The extract is washed with water, an aqueous solution of sodium hydrogen carbonate, an aqueous solution of sodium chloride, etc. and dried over anhydrous sodium sulfate, etc. After the solvent is evaporated, the resulting residue is purified by silica-gel column chromatography, thin-layer chromatography, high-performance preparative liquid chromatography, recrystallization, etc.

In the case where a salt of Compound (I) is desired and it is obtained in the form of the desired salt, it can be subjected to purification as such. In the case where Compound (I) is obtained in the free state and its salt is desired, the desired salt can be obtained by dissolving or suspending Compound (I) in a suitable solvent and adding a suitable acid to the solution or suspension.

The reaction intermediates may be directly used in the subsequent step without isolation or purification. Compounds (I) and its pharmaceutically acceptable salts may be in the form of adducts with water or various solvents, which are also within the scope of the present invention. Further, all possible isomers of Compounds (I) including optical isomers and mixtures thereof also fall within the scope of the present invention.

The structures and compound numbers of representative compounds which fall under Compounds (I) are shown in Table 1. The structures and compound numbers of the synthetic intermediates of Compound (I) are shown in Table 2.

TABLE 1

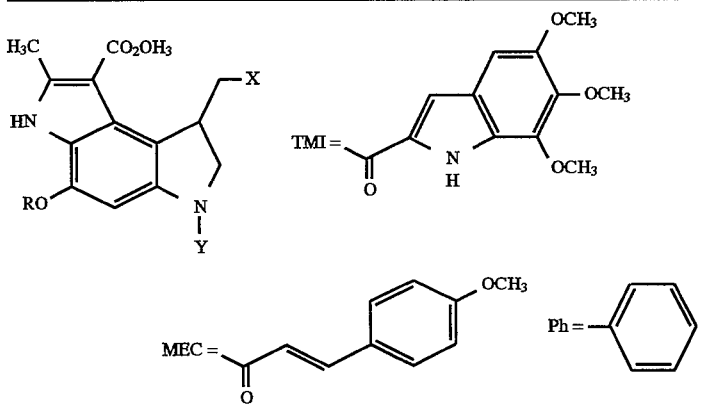

| Compound No. | R | X | Y |
|---|---|---|---|
| 1 | CH$_2$Ph | Br | TMI |
| 2 | CH$_3$ | Br | TMI |
| 3 | CH$_3$ | Cl | TMI |
| 4 | SO$_2$CH$_3$ | Br | TMI |
| 5 | SO$_2$CF$_3$ | Br | TMI |
| 6 | COCH$_3$ | Br | TMI |
| 7 | CO$_2$CH$_3$ | Br | TMI |
| 8 | CO$_2$Ph | Br | TMI |
| 9 | CONHCH$_2$CO$_2$CH$_2$Ph | Br | TMI |
| 10 | CONHCH$_2$CO$_2$H | Br | TMI |
| 11 | CONHCH(CH$_2$Ph)CO$_2$H | Br | TMI |
| 12 | CO$_2$CH$_3$ | Br | MEC |
| 13 | CONHCH$_2$CO$_2$H | Br | MEC |
| 14 | COCH$_3$ | Br | MEC |
| 15 | COSCH$_3$ | Br | MEC |
| 16 | CO-(pyridyl) | Br | MEC |

TABLE 1-continued
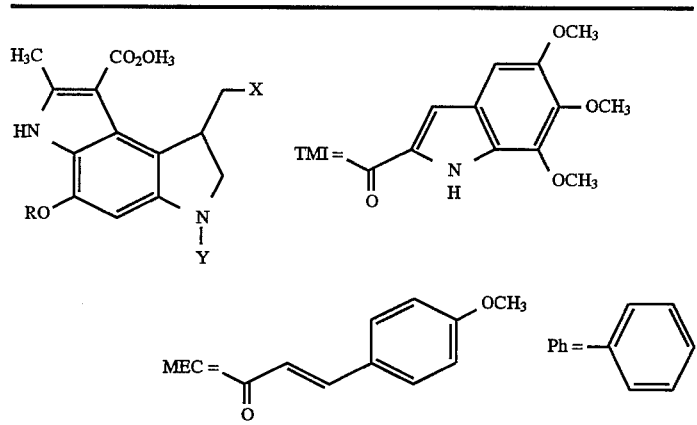
| Compound No. | R | X | Y |
|---|---|---|---|
| 17 | CO—⟨phenyl⟩—N·HCl | Br | MEC |
| 18 | CONHN⟨piperazine⟩NCH₃ | Br | MEC |
| 19 | CONHN⟨piperazine⟩NCH₃·HCl | Br | MEC |
| 20 | CONHN⟨morpholine⟩O | Br | MEC |
| 21 | CO—⟨pyrazine with H₂N⟩ | Br | MEC |
| 22 | CO—⟨phenyl⟩—NH₂, NH₂ | Br | MEC |
| 23 | CO—⟨phenyl⟩—N(CH₃)₂ | Br | MEC |
| 24 | CO—⟨phenyl⟩—N(CH₃)₂ | Br | MEC |
| 25 | CO—⟨phenyl⟩—N(C₂H₅)₂ | Br | MEC |

TABLE 1-continued

Structures:
- Main scaffold: H3C, CO2OH3, HN, RO, with substituents X and Y on indoline
- TMI = 2-(4,5,7-trimethoxyindol-2-yl)carbonyl group (4,5,7-OCH3 on indole-NH, with C=O linker)
- MEC = (E)-3-(4-methoxyphenyl)acryloyl group (O=C-CH=CH-C6H4-OCH3)
- Ph = phenyl

| Compound No. | R | X | Y |
|---|---|---|---|
| 26 | CO—C6H4—N(pyrrole) | Br | MEC |
| 27 | CO—C6H4—CH2N(piperazine)NCH3 | Br | MEC |
| 28 | CO—C6H4—CH2N(piperazine)NCH3·HBr | Br | MEC |
| 29 | CONHN(CH3)2 | Br | MEC |
| 30 | CON(CH3)NH2 | Br | MEC |
| 31 | CONHN(piperidine)—N(piperidine) | Br | MEC |
| 32 | CONHN(piperidine)—N(piperidine)·HBr | Br | MEC |
| 33 | COCH2SCH2CO2H | Br | MEC |
| 34 | CO—C6H4—CH2NHCOOC(CH3)3 | Br | MEC |
| 35 | CO—C6H4—CH2NH2 | Br | MEC |
| 36 | CO—C6H4—CH2NH2·HBr | Br | MEC |
| 37 | CONHN(piperazine)NCH3·HBr | Br | MEC |
| 38 | CON(CH3)NHCH3 | Br | MEC |

TABLE 1-continued

[Structure: indoline derivative with H3C, CO2OH3, HN, RO, X, N-Y substituents]

TMI = [3,4,5-trimethoxyindole-2-carbonyl group structure]

MEC = [4-methoxycinnamoyl group structure]

Ph = [phenyl group]

| Compound No. | R | X | Y |
|---|---|---|---|
| 39 | COCH₂N(piperazine)NCH₃·2HBr | Br | MEC |
| 40 | COCH₂N(piperidine)—N(piperidine)·2HBr | Br | MEC |

TABLE 2

[Structure of compound with H3C, CO2CH3, HN, RO, OH, and TMI-like substituent]

Ph = [phenyl]

| Compound No. | R |
|---|---|
| a | H |
| b | CH₂Ph |
| c | CH₃ |

The pharmacological activity of representative Compounds (I) is shown in Test Examples.

TEST EXAMPLE

1. Growth Inhibitory Effect Against HeLaS₃ cells

HeLaS₃ cells were suspended in MEM medium containing 10% fetal calf serum and 2 mM glutamine to a concentration of $2.67 \times 10^4$ cells/ml. The cell suspension thus prepared was put into wells of a 24-well culture plate in an amount of 0.75 ml per well. After the cells were incubated in a $CO_2$ incubator overnight at 37° C., Compound (I) which had been appropriately diluted with a culture medium was added to each well in an amount of 0.25 ml.

The cells were further incubated in the $CO_2$ incubator for 72 hours, and the culture supernatant was removed. Then, the cells were dispersed in a solution of trypsin and EDTA, and recovered. The number of the cells was counted using a cell counter. The concentration of Compound (I) at which the growth of the cells is inhibited by 50% was calculated by comparing the number of untreated cells with the number of the cells treated with Compound (I) at known concentrations, and the value was defined as $IC_{50}$.

The result is shown in Table 3.

2. Therapeutic Effect on Sarcoma 180 Tumor

Five male ddY-strain mice each weighing 18–20 g were used for each group as test animals, and $5 \times 10^5$ Sarcoma 180 tumor cells were implantedat the axilla subcutaneously. One day after the implantation, 0.2 ml of a physiological saline containing Compound (I) at the concentration shown in Table 3 was intravenously administered to each mouse. T/C [T: average tumor volume ($mm^3$) of the group treated with the test compound, C: average tumor volume ($mm^3$) of the control group (to which 0.2 ml of a physiological saline was intravenously administered)] was determined seven days after the implantation.

The result is shown in Table 3.

TABLE 3

| Compound No. | $IC_{50}$ (nM) | Dose (mg/kg) | T/C |
|---|---|---|---|
| 1 | 5.1 | 8.0 | 0.19 |
| 2 | 6.3 | 8.0 | 0.27 |
| 4 | 4.0 | 16 | 0.20 |
| 6 | 0.13 | 0.50 | 0.18 |
| 7 | 0.082 | 0.50 | 0.10 |
| 8 | 0.051 | 0.50 | 0.090 |
| 10 | 0.23 | 4.0 | 0.10 |
| 11 | 0.17 | 4.0 | 0.07 |
| 13 | 0.98 | 12 | 0.33 |
| 14 | 0.31 | 4.0 | 0.22 |
| 15 | 0.43 | 1.0 | 0.36 |

TABLE 3-continued

| Compound No. | IC$_{50}$ (nM) | Dose (mg/kg) | T/C |
|---|---|---|---|
| 16 | 0.40 | 2.0 | 0.33 |
| 18 | 0.54 | 8.0 | 0.18 |
| 19 | 0.53 | 4.0 | 0.26 |
| 20 | 6.7 | | |
| 21 | 0.38 | | |
| 22 | 2.7 | | |
| 24 | 0.43 | 2.0 | 0.31 |
| 25 | 13 | 2.0 | 0.14 |
| 26 | 1.7 | 2.0 | 0.15 |
| 28 | 0.83 | 2.0 | 0.21 |
| 29 | 0.43 | 2.0 | 0.18 |
| 30 | 0.94 | 2.0 | 0.22 |
| 32 | 0.80 | 8.0 | 0.10 |
| 33 | 0.33 | 2.0 | 0.17 |
| 34 | 0.52 | 2.0 | 0.28 |
| 36 | 1.0 | 4.0 | 0.35 |
| 37 | 0.91 | 8.0 | 0.27 |
| 38 | 1.5 | 4.0 | 0.14 |
| 39 | 0.36 | | |
| 40 | 0.29 | | |

3. Acute toxicity

Compound (I) was intravenously administered to ddY-strain male mice each weighing 20±1 g. MLD (minimum lethal dose) was determined by observing the mortality at 14 days after administration. The result is shown in Table 4.

TABLE 4

| Compound No. | MLD (mg/kg) |
|---|---|
| 6 | 0.25 |
| 7 | 0.50 |
| 8 | 0.50 |
| 10 | >4.0 |
| 11 | >4.0 |
| 13 | 2.0 |
| 14 | 2.0 |
| 19 | >8.0 |
| 25 | 2.0 |
| 26 | 2.0 |
| 28 | 2.0 |
| 29 | 2.0 |
| 30 | 2.0 |
| 32 | >8.0 |
| 33 | 2.0 |
| 37 | >8.0 |
| 38 | 4.0 |
| 39 | 4.0 |
| 40 | 2.0 |

Compounds (I) and pharmaceutically acceptable salts thereof can be used as anti-tumor compositions singly or in combination with at least one pharmaceutically acceptable auxiliary. For example, Compounds (I) or salts thereof are dissolved in a physiological saline or in an aqueous solution of glucose, lactose, mannitol, etc. to prepare a pharmaceutical composition suitable for injection. Alternatively, Compounds (I) or salts thereof are freeze-dried in a conventional manner and mixed with sodium chloride to prepare a powder injection. If necessary, the pharmaceutical composition of the present invention may contain additives which are known in the art of medical preparation, for example, pharmaceutically acceptable salts.

Although the dose of the composition of the present invention varies depending on the age, condition, etc. of a patient, Compound (I) is administered to mammals including human beings at a dose of 0.01 to 60 mg/kg/day. Administration may be conducted, for example, once a day (single administration or consecutive administrations) or intermittently 1 to 3 times a week or once every 2 to 3 weeks, intravenously. If desired, intraarterial administration, intraperitoneal administration, intrathoracial administration, etc. are also possible at a similar dose and in a similar manner. Further, if desired, the composition may also be administered orally, in a similar dose and in a similar manner. Forms for oral administration include tablets, capsules, powders, granules and ampoules, which contain pharmaceutical auxiliaries well known in the art of medical preparation.

The present invention is illustrated by referring to the following Examples. The physicochemical properties shown in the following Examples were determined with the following equipment.

| NMR | JEOL, Ltd. | FX-100 (100 MHz) |
|---|---|---|
| | | JNM-GX270 (270 MHz) |
| | | JNM-EX270 (270 MHz) |
| | Bruker | AM-400 (400 MHz) |
| | | AM-500 (500 MHz) |
| MS | Hitachi Ltd. | M-80B |
| | Shimadzu | QP-1000 |
| | JEOL, Ltd. | JMS-D300 |
| | | JMS-SX102 |
| IR | Japan Spectral Co., Ltd. | IR-810 |
| | HORIBA | FT200 |

In thin-layer chromatography, a silica-gel plate (Silica gel 60F$_{254s}$ 0.5 mm 20×20 cm) manufactured by Merck Co. was used. As the silica gel, Wakogel C-200 manufactured by Wako Pure Chemical Industries, Ltd. was used.

BEST MODE FOR CARRYING OUT THE INVENTION

EXAMPLE 1

Synthesis of Compound 1

Compound b (17 mg, 0.028 mmol) obtained in Reference Example 2 was dissolved in 1 ml of pyridine, and 0.0065 ml (0.084 mmol) of methanesulfonyl chloride was added thereto. The mixture was stirred at room temperature for 2 hours. To the reaction mixture was added a 0.01M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. The obtained crude product was dissolved in 1 ml of N,N-dimethylformamide, and 7.3 mg (0.084 mmol) of lithium bromide was added thereto. The mixture was stirred at 80° C. for 2 hours. To the resulting reaction mixture was added a 0.01M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. The obtained crude product was purified by silica-gel column chromatography (20 ml of silica gel, n-hexane: ethyl acetate=2:1) to give 12 mg of Compound 1 (yield: 64%).

The physicochemical properties of Compound 1 are as follows.

$^1$H-NMR (400 MHz, CDCl$_3$) δ (ppm); 9.38 (1H, br s), 8.62 (1H, br s), 8.16 (1H, s), 7.51–7.36 (5H, m), 7.01 (1H, d, J=2.3Hz), 6.90 (1H, s), 5.27 (1H, d, J=11.0Hz), 5.22 (1H, d, J=11.0Hz), 4.75 (1H, br d, J=8.9Hz), 4.56 (2H, m), 4.08 (3H, s), 3.97 (3H, s), 3.95 (3H, s), 3.93 (3H, s), 3.82 (1H, dd, J=8.1, 2.1Hz), 3.22 (1H, dd, J=8.1, 8.1Hz), 2.72 (3H, s)

IR (KBr) ν (cm⁻¹); 1697, 1605, 1525, 1494, 1415, 1214, 1112, 1088

SIMS (m/z); 664, 662 (M+H) $^+$, 430, 428, 234

EXAMPLE 2

Synthesis of Compound 2

Compound c (52 mg, 0.089 mmol) obtained in Reference Example 3 was dissolved in 2.6 ml of pyridine, and 0.014 ml (0.181 mmol) of methanesulfonyl chloride was added thereto. The mixture was stirred at room temperature for 2 hours. To the reaction mixture was added a 0.01M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. The obtained crude product was dissolved in 2.6 ml of N,N-dimethylformamide, and 15.5 mg (0.178 mmol) of lithium bromide was added thereto. The mixture was stirred at 80° C. for 3 hours. To the resulting reaction mixture was added a 0.01M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. The obtained crude product was purified by silica-gel column chromatography (20 ml of silica gel, n-hexane: ethyl acetate=1:1) to give 48 mg of Compound 2 (yield: 92%).

The physicochemical properties of Compound 2 are as follows.

$^1$H-NMR (400 MHz, CDCl$_3$) δ (ppm); 9.38 (1H, br s), 8.59 (1H, br s), 8.02 (1H, s), 7.01 (1H, d, J=2.3Hz), 6.90 (1H, s), 4.74 (1H, br d, J=8.9Hz), 4.54 (2H, m), 4.08 (3H, s), 4.01 (3H, s), 3.97 (3H, s), 3.95 (3H, s), 3.92 (3H, s), 3.82 (1H, dd, J=9.8, 3.9Hz), 3.21 (1H, dd, J=9.9, 9.9Hz), 2.73 (3H, s)

IR (KBr) ν (cm⁻¹); 1697, 1584, 1492, 1411, 1312, 1215, 1112

SIMS (m/z); 588, 586 (M+H)$^+$, 354 352 234

EXAMPLE 3

Synthesis of Compound 3

Compound c (25 mg, 0.048 mmol) obtained in Reference Example 3 was dissolved in 2.0 ml of pyridine, and 0.019 ml (0.25 mmol) of methanesulfonyl chloride was added thereto. The mixture was stirred at room temperature for 24 hours. To the reaction mixture was added 1N hydrochloric acid, and the mixture was extracted with ethyl acetate. The ethyl acetate layer was washed with a saturated aqueous solution of sodium hydrogen carbonate and a saturated aqueous solution of sodium chloride, dried over anhydrous sodium sulfate, and concentrated under reduced pressure. The obtained crude product was dissolved in 2.0 ml of N,N-dimethylformamide, and 11.0 mg (0.259 mmol) of lithium chloride was added thereto. The mixture was stirred at 80° C. for 3 hours. To the resulting reaction mixture was added a 0.01M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. The obtained crude product was purified by silica-gel column chromatography (20 ml of silica gel, n-hexane: ethyl acetate=3:1) to give 19 mg of Compound 3 (yield: 73%).

The physicochemical properties of Compound 3 are as follows.

$^1$H-NMR (400 MHz, CDCl$_3$) δ (ppm); 9.42 (1H, s), 8.70 (1H, s), 8.03 (1H, s), 7.00 (1H, d, J=2.3Hz), 6.89 (1H, s), 4.75 (1H, br d, J=9.5Hz), 4.52 (1H, dd, J=9.5, 8.4Hz), 4.47 (1H, m), 4.07 (3H, s), 4.00 (3H, s), 3.95 (3H, s), 3.95 (3H, s), 3.94 (1H, m), 3.92 (3H, s), 3.33 (1H, dd, J=10.1, 9.9Hz), 2.73 (3H, s)

IR (KBr) ν (cm⁻¹); 1685, 1631, 1521, 1457, 1405, 1313, 1220, 1113

SIMS (m/z); 542 (M+H) $^+$, 234

EXAMPLE 4

Synthesis of Compound 4

Compound E (30 mg, 0.044 mmol) was dissolved in 1.5 ml of tetrahydrofuran (THF), and 1.5 ml of a 1N hydrobromic acid aqueous solution was added thereto. The mixture was stirred at room temperature for 24 hours. To the reaction mixture was added a 1N hydrobromic acid aqueous solution, and the resulting mixture was extracted with chloroform. The chloroform layer was dried over anhydrous sodium sulfate, and concentrated under reduced pressure. The obtained crude product was dissolved in 2 ml of methylene chloride. Then, 0.016 ml (0.21 mmol) of methanesulfonyl chloride and 0.029 ml (0.21 mmol) of triethylamine were added thereto. The mixture was stirred at −78° C. for 2 hours. To the reaction mixture was added phosphate buffer (pH 7), and the mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, chloroform:methanol= 100:1) to give 25 mg of Compound 4 (yield: 87%).

The physicochemical properties of Compound 4 are as follows.

$^1$H-NMR (400 MHz, CDCl$_3$) δ (ppm); 9.36 (1H, br s), 9.00 (1H, br s), 8.31 (1H, s), 7.01 (1H, d, J=2.2Hz), 6.90 (1H, s), 4.77 (1H, dd, J=10.5, 1.0Hz), 4.68 (1H, m), 4.57 (1H, dd, J=10.4, 9.6Hz), 4.08 (3H, s), 3.98 (3H, s), 3.95 (3H, s), 3.92 (3H, s), 3.81 (1H, dd, J=10.1, 2.5Hz), 3.33 (1H, s), 3.26 (1H, dd, J=9.9, 9.9Hz), 2.75 (3H, s)

IR (KBr) ν (cm⁻¹); 1698, 1522, 1410, 1364, 1217, 1177, 1106

SIMS (m/z); 652, 650 (M+1) $^+$, 418 416, 234

EXAMPLE 5

Synthesis of Compound 5

Compound E (100 mg, 0.15 mmol) was dissolved in 5 ml of tetrahydrofuran, and 0.220 ml (0.22 mmol) of a tetrahydrofuran solution (1.0M) of tetra-n-butylammonium fluoride was added thereto. The mixture was stirred at room temperature for 1 hour. To the reaction mixture was added a 0.2M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. To the reaction mixture were added 5 ml of acetonitrile and 0.5 ml of 48% hydrobromic acid, and the mixture was stirred for 1 hour. To the reaction mixture was added a 1N hydrobromic acid aqueous solution, and the mixture was extracted with chloroform. The chloroform layer was dried over anhydrous sodium sulfate, and concentrated under reduced pressure. The obtained crude product was dissolved in 5 ml of methylene chloride, and 0.075 ml (0.45 mmol) of trifluoromethanesulfonic anhydride and 0.063 ml (0.45 mmol) of triethylamine were added thereto at −78° C. The mixture was stirred at −78° C. for 2 hours. To the reaction mixture was added phosphate buffer (pH 7), and the mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, hexane:ethyl acetate=3:1) to give 77 mg of Compound 5 (yield: 73%).

The physicochemical properties of Compound 5 are as follows.

$^1$H-NMR (400 MHz, CDCl$_3$) δ (ppm); 9.39 (1H, s), 8.74 (1H, s), 8.45 (1H, s), 7.00 (1H, d, J=2.3Hz), 6.89 (1H, s), 4.78 (1H, dd, J=10.5, 1.3Hz), 4.69 (1H, m), 4.58 (1H, dd, J=10.2, 9.2Hz), 4.08 (3H, s), 3.99 (3H, s), 3.95 (3H, s), 3.92 (3H, s), 3.79 (1H, dd, J=10.1, 2.4Hz), 3.26 (1H, dd, J=10.0, 10.0Hz), 2.78 (3H, s)

IR (KBr) ν (cm$^{-1}$); 1697, 1611, 1522, 1412, 1311, 1213, 1137, 1114

SIMS (m/z); 706, 704 (M+H) $^+$, 234

EXAMPLE 6

Synthesis of Compound 6

Compound E (40 mg, 0.058 mmol) was dissolved in 4 ml of tetrahydrofuran, and 0.087 ml (0.087 mmol) of a tetrahydrofuran solution (1.0M) of tetra-n-butylammonium fluoride was added thereto. The mixture was stirred at room temperature for 1 hour. To the reaction mixture was added a 0.2M phosphate buffer (pH 7), and the mixture was extracted with ethyl acetate. The ethyl acetate layer was washed with a saturated aqueous solution of sodium chloride, dried over anhydrous sodium sulfate, and concentrated under reduced pressure. To the reaction mixture were added 4 ml of acetonitrile and 2 ml of 48% hydrobromic acid, and the mixture was stirred for 1 hour. To the reaction mixture was added a 1N hydrobromic acid aqueous solution, and the mixture was extracted with chloroform. The chloroform layer was dried over anhydrous sodium sulfate, and concentrated under reduced pressure. The obtained crude product was dissolved in 4 ml of methylene chloride, and 0.020 ml (0.21 mmol) of acetic anhydride and 25 mg (0.20 mmol) of dimethylaminopyridine were added thereto at 0° C. The mixture was stirred at 0° C. for 2 hours. To the reaction mixture was added phosphate buffer (pH 7), and the mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, chloroform:methanol=50:1) to give 23 mg of Compound 6 (yield: 65%).

The physicochemical properties of Compound 6 are as follows.

$^1$H-NMR (400 MHz, CDCl$_3$) δ (ppm); 9.35 (1H, br s), 8.45 (1H, s), 8.20 (1H, s), 6.99 (1H, d, J=2.2Hz), 6.89 (1H, s), 4.75 (1H, br d, J=9.6Hz), 4.62 (1H, m), 4.55 (1H, br d, J=9.8Hz), 4.08 (3H, s), 3.96 (3H, s), 3.95 (3H, s), 3.92 (3H, s), 3.81 (1H, dd, J=10.0, 2.4Hz), 3.24 (1H, dd, J=10.0, 10.0Hz), 2.72 (3H, s), 2.41 (3H, s)

IR (KBr) ν (cm$^{-1}$); 1686, 1654, 1559, 1507, 1457, 1314, 1189

SIMS (m/z); 616, 614 (M+H) $^+$, 234

EXAMPLE 7

Synthesis of Compound 7

Compound E (40 mg, 0.058 mmol) was dissolved in 4 ml of tetrahydrofuran, and 0.088 ml (0.088 mmol) of a tetrahydrofuran solution (1.0M) of tetra-n-butylammonium fluoride was added thereto. The mixture was stirred at room temperature for 1 hour. To the reaction mixture was added a 0.2M phosphate buffer of pH 7, and the mixture was extracted with chloroform. The chloroform layer was washed with a saturated aqueous solution of sodium chloride, dried over anhydrous sodium sulfate, and concentrated under reduced pressure. To the obtained crude product were added 4 ml of acetonitrile and 2 ml of 48% hydrobromic acid, and the mixture was stirred at room temperature for 1 hour. To the reaction mixture was added a 1N hydrobromic acid aqueous solution, and the resulting mixture was extracted with chloroform. The chloroform layer was dried over anhydrous sodium sulfate, and concentrated under reduced pressure. The obtained crude product was dissolved in 2.5 ml of methylene chloride, and 0.014 ml (0.18 mmol) of methyl chloroformate and 0.025 ml (0.18 mmol) of triethylamine were added thereto at −78° C. The mixture was stirred at −78° C. to 0° C. for 2 hours. To the reaction mixture was added a 0.2M phosphate buffer (pH 7), and the mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, n-hexane:ethyl acetate=2:1) to give 32 mg of Compound 7 (yield: 87%).

The physicochemical properties of Compound 7 are as follows.

$^1$H-NMR (270 MHz, CDCl$_3$) δ (ppm); 9.39 (1H, s), 8.74 (1H, s), 8.33 (1H, s), 7.00 (1H, d, J=2.0Hz), 6.90 (1H, s), 4.75 (1H, br d, J=9.4Hz), 4.58 (2H, m), 4.08 (3H, s), 3.97 (3H, s), 3.96 (3H, s), 3.95 (3H, s), 3.92 (3H, s), 3.72 (1H, m), 3.24 (1H, dd, J=9.9, 9.4Hz), 2.72 (3H, s)

IR (KBr) ν (cm$^{-1}$); 1768, 1696, 1617, 1495, 1442, 1315, 1263, 1219, 1111

FABMS (m/z); 632, 630 (M+H) $^+$, 234

EXAMPLE 8

Synthesis of Compound 8

Compound E (50 mg, 0.07 mmol) was dissolved in 5 ml of tetrahydrofuran, and 0.11 ml (0.11 mmol) of a tetrahydrofuran solution (1.0M) of tetra-n-butylammonium fluoride was added thereto. The mixture was stirred at room temperature for 1 hour. To the reaction mixture was added a 0.2M phosphate buffer of pH 7, and the mixture was extracted with chloroform. The chloroform layer was washed with a saturated aqueous solution of sodium chloride, dried over anhydrous sodium sulfate, and concentrated under reduced pressure. To the obtained crude product were added 5 ml of acetonitrile and 2.5 ml of 48% hydrobromic acid, and the mixture was stirred at room temperature for 1 hour. To the reaction mixture was added a 1N hydrobromic acid aqueous solution, and the resulting mixture was extracted with chloroform. The chloroform layer was dried over anhydrous sodium sulfate, and concentrated under reduced pressure. The obtained crude product was dissolved in 3 ml of methylene chloride, and 0.027 ml (0.22 mmol) of phenyl chloroformate and 0.030 mg (0.22 mmol) of triethylamine were added thereto at −78° C. The mixture was stirred at −78° C. to 0° C. for 1 hour. To the reaction mixture was added a 0.2M phosphate buffer (pH 7), and the mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, n-hexane:ethyl acetate=2:1) to give 40 mg of Compound 8 (yield: 82%).

The physicochemical properties of Compound 8 are as follows.

$^1$H-NMR (270 MHz, CDCl$_3$) δ (ppm); 9.39 (1H, s), 8.84 (1H, s), 8.45 (1H, s), 7.46–7.29 (5H, m), 7.00 (1H, d, J=1.9Hz), 6.90 (1H, s), 4.76 (1H, br d, J=9.4Hz), 4.59 (2H, m), 4.08 (3H, s), 3.98 (3H, s), 3.95 (3H, s), 3.92 (3H, s), 3.72 (1H, m), 3.24 (1H, dd, J=9.9, 9.4Hz), 2.75 (3H, s)

IR (KBr) ν (cm$^{-1}$); 1780, 1614, 1493, 1464, 1414, 1313, 1221, 1188, 1111

FABMS (m/z); 694, 692 (M+H) $^+$, 234

EXAMPLE 9

Synthesis of Compound 9

Compound E (20 mg, 0.03 mmol) was dissolved in 1 ml of tetrahydrofuran, and 0.045 ml (0.045 mmol) of a tetrahydrofuran solution (1.0M) of tetra-n-butylammonium fluoride was added thereto. The mixture was stirred at room temperature for 1 hour. To the reaction mixture was added a 0.2M phosphate buffer of pH 7, and the mixture was extracted with chloroform. The chloroform layer was washed with a saturated aqueous solution of sodium chloride, dried over anhydrous sodium sulfate, and concentrated under reduced pressure. To the obtained crude product were added 1 ml of acetonitrile and 0.5 ml of 48% hydrobromic acid, and the mixture was stirred at room temperature for 2 hours. To the reaction mixture was added a 1N hydrobromic acid aqueous solution, and the resulting mixture was extracted with chloroform. The chloroform layer was dried over anhydrous sodium sulfate, and concentrated under reduced pressure. The obtained crude product was dissolved in 1 ml of methylene chloride, and 19 mg (0.09 mmol) of p-nitrophenyl chloroformate and 0.013 mg (0.09 mmol) of triethylamine were added thereto at −78° C. The mixture was stirred for 30 minutes. To the reaction mixture were added 36 mg (0.11 mmol) of glycine benzyl ester p-toluenesulfonate and 0.015 ml (0.11 mmol) of triethylamine, and the mixture was stirred at −78° C. to 0° C. for 2 hours. To the reaction mixture was added a saturated aqueous solution of sodium hydrogen carbonate, and the resulting mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (20 ml of silica gel, chloroform:methanol=50:1) to give 15 mg of Compound 9 (yield: 65%).

The physicochemical properties of Compound 9 are as follows.

$^1$H-NMR (270 MHz, CDCl$_3$) δ (ppm); 9.34 (1H, br), 9.31 (1H, s), 8.10 (1H, br), 7.28–7.18 (5H, m), 6.91 (1H, d, J=2.0Hz), 6.81 (1H, s), 5.82 (1H, t, J=5.6Hz), 5.09 (2H, s), 4.99 (2H, t, J=5.5Hz), 4.65 (1H, br d, J=10.0Hz), 4.47 (2H, m), 4.00 (3H, s), 3.95 (3H, s), 3.86 (3H, s), 3.84 (3H, s), 3.71 (1H, br d, J=7.2Hz), 3.14 (1H, dd, J=9.9, 9.6Hz) 2.57 (3H, s)

IR (KBr) ν (cm$^{-1}$); 1741, 1583, 1495, 1456, 1414, 1290, 1213, 1190

FABMS (m/z); 765, 763 (M+H) $^+$, 234

EXAMPLE 10

Synthesis of Compound 10

Compound 9 (15 mg, 0.02 mmol) obtained in Example 9 was dissolved in a mixture of 0.5 ml of ethanol, 0.1 ml of methanol and 0.1 ml of a 1N hydrobromic acid aqueous solution, and 4 mg of 10% Pd/C was added thereto. The mixture was stirred in a hydrogen atmosphere at room temperature for 2 hours. The reaction mixture was filtered, and the filtrate was concentrated under reduced pressure. Water was added to the obtained crude product, and the mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (20 ml of silica gel, chloroform:methanol:acetic acid= 100:10:2) to give 12 mg of Compound 10 (yield: 89%).

The physicochemical properties of Compound 10 are as follows.

$^1$H-NMR (270 MHz, acetone-d$_6$+trifluoroacetic acid-d) δ (ppm); 8.04 (1H, s), 6.98 (1H, s), 6.87 (1H, s), 5.40 (1H, br), 4.54 (2H, m), 3.91 (3H, s), 3.78 (3H, s), 3.77 (1H, m), 3.75 (3H, s), 3.74 (3H, s), 3.74 (1H, m), 2.57 (3H, s)

IR (KBr) ν (cm$^{-1}$); 1697, 1601, 1444, 1416, 1219, 1109, 1088

FABMS (m/z); 675, 673 (M+H) $^+$, 234

EXAMPLE 11

Synthesis of Compound 11

Compound E (20 mg, 0.03 mmol) was dissolved in 1 ml of tetrahydrofuran, and 0.045 ml (0.045 mmol) of a tetrahydrofuran solution (1.0M) of tetra-n-butylammonium fluoride was added thereto. The mixture was stirred at room temperature for 1 hour. To the reaction mixture was added a 0.2M phosphate buffer of pH 7, and the mixture was extracted with chloroform. The chloroform layer was washed with a saturated aqueous solution of sodium chloride, dried over anhydrous sodium sulfate, and concentrated under reduced pressure. To the obtained crude product were added 1 ml of acetonitrile and 0.5 ml of 48% hydrobromic acid, and the mixture was stirred at room temperature for 2 hours. To the reaction mixture was added a 1N hydrobromic acid aqueous solution, and the resulting mixture was extracted with chloroform. The chloroform layer was dried over anhydrous sodium sulfate, and concentrated under reduced pressure. The obtained crude product was dissolved in 1 ml of methylene chloride, and 19 mg (0.09 mmol) of p-nitrophenyl chloroformate and 0.013 ml (0.09 mmol) of triethylamine were added thereto at −78° C. The mixture was stirred for 30 minutes. To the reaction mixture were added 18 mg (0.11 mmol) of phenylalanine and 0.013 ml (0.09 mmol) of triethylamine, and the mixture was stirred at −78° C. to room temperature for 24 hours. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (20 ml of silica gel, chloroform:methanol:acetic acid=100:5:1) to give 8 mg of Compound 11 (yield: 35%).

The physicochemical properties of Compound 11 are as follows.

$^1$H-NMR (270 MHz, DMSO-d$_6$) δ (ppm); 12.35 (1H, br), 11.38 (1H, br s), 7.81 (2H, s), 7.27–7.16 (5H, m), 6.95 (1H, d, J=2.2Hz), 6.93 (1H, s), 4.58 (1H, m), 4.41 (3H, m), 4.15 (1H, m), 3.88 (3H, s), 3.79 (3H, s), 3.77 (3H, s), 3.74 (3H, s), 3.54 (3H, m), 2.98 (1H, m), 2.62 (3H, s)

IR (KBr) ν (cm$^{-1}$); 1699, 1525, 1416, 1313, 1217, 1111

FABMS (m/z); 765, 763 (M+H) $^+$, 573 571 234

EXAMPLE 12

Synthesis of Compound 12

Acetonitrile (1.5 ml) and 0.135 ml of 48% hydrobromic acid were added to 33 mg (0.079 mmol) of Compound D, and the mixture was stirred at room temperature for 1 hour. To the reaction mixture was added a 1N hydrobromic acid aqueous solution, and the mixture was extracted with chloroform. The chloroform layer was dried over anhydrous sodium sulfate, and concentrated under reduced pressure. The obtained crude product was dissolved in 3.5 ml of methylene chloride, and 0.019 ml (0.25 mmol) of methyl chloroformate and 0.033 ml (0.24 mmol) of triethylamine were added thereto at −78° C. The mixture was stirred for 3 hours. To the reaction mixture was added a 0.2M phosphate buffer of pH 7, and the resulting mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, chloroform:methanol=50:1) to give 40 mg of Compound 12 (yield: 72%).

The physicochemical properties of Compound 12 are as follows.

$^1$H-NMR (270 MHz, CDCl$_3$) δ (ppm); 8.86 (1H, br), 8.40 (1H, br), 7.80 (1H, d, J=15.1Hz), 7.57 (1H, d, J=8.9Hz), 6.93 (1H, d, J=8.8Hz), 6.80 (1H, d, J=15.2Hz), 6.79 (1H, br s), 4.54 (1H, m), 4.47 (1H, br d, J=10.9Hz), 4.31 (1H, dd, J=9.6, 9.6Hz), 3.96 (3H, s), 3.93 (3H, s), 3.86 (3H, s), 3.79 (1H, br d, J=10.5Hz), 3.22 (1H, dd, J=10.5, 10.5Hz), 2.67 (3H, s)

IR (KBr) ν (cm$^{-1}$); 1768, 1697, 1645, 1512, 1437, 1412, 1252, 1217, 1095

FABMS (m/z); 559, 557 (M) $^+$

EXAMPLE 13

Synthesis of Compound 13

Acetonitrile (3.5 ml) and 0.29 ml of 48% hydrobromic acid were added to 70 mg (0.17 mmol) of Compound D, and the mixture was stirred at room temperature for 1 hour. To the reaction mixture was added a 1N hydrobromic acid aqueous solution, and the mixture was extracted with chloroform. The chloroform layer was dried over anhydrous sodium sulfate, and concentrated under reduced pressure. The crude product was dissolved in 7 ml of methylene chloride, and 103 mg (0.51 mmol) of p-nitrophenyl chloroformate and 0.071 ml (0.51 mmol) of triethylamine were added thereto at −78° C. The mixture was stirred for 30 minutes. To the reaction mixture were added 100 mg (0.58 mmol) of glycine tert-butyl ester hydrochloride and 0.083 ml (0.60 mmol) of triethylamine, and the mixture was stirred at −78° C. to room temperature for 9 hours. To the reaction mixture was added a 0.2M phosphate buffer of pH 7, and the resulting mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (30 ml of silica gel, chloroform:methanol=20:1) to give 110 mg of a tert-butyl ester of Compound 13 (yield: 85%). Ethylene dichloride (8 ml) was added to the tert-butyl ester of Compound 13 (80 mg, 0.10 mmol), and 0.18 ml of 48% hydrobromic acid was added thereto. The mixture was stirred at 50° C. for 4 hours. To the reaction mixture was added a 1N hydrobromic acid aqueous solution, and the mixture was extracted with chloroform. The chloroform layer was dried over anhydrous sodium sulfate, and concentrated under reduced pressure. The obtained crude product was purified by silica-gel chromatography (preparative T.L.C., chloroform:methanol:acetic acid=50:10:1) to give 23 mg of Compound 13 (yield: 32%).

The physicochemical properties of Compound 13 are as follows.

1N-NMR (270 MHz, acetone d$_6$+trifluoroacetic acid-d) δ (ppm); 8.17 (1H, br), 7.68 (1H, d, J=15.5Hz), 7.60 (2H, d, J=8.9Hz), 7.03 (1H, d, J=15.4Hz), 6.89 (2H, d, J=8.9Hz), 4.49 (2H, m), 3.96 (2H, s), 3.93 (1H, m), 3.83 (3H, s), 3.78 (1H, m), 3.76 (3H, s), 3.37 (1H, m), 2.61 (3H, s)

IR (KBr) ν (cm$^{-1}$); 1700, 1647, 1572, 1560, 1412, 1221, 1109

FABMS (m/z); 708, 706 (M) $^+$

EXAMPLE 14

Synthesis of Compound 14

Acetonitrile (1.3 ml) and 0.27 ml of 48% hydrobromic acid were added to 13 mg (0.031 mmol) of Compound D, and the mixture was stirred at room temperature for 1 hour. To the reaction mixture was added a 1N hydrobromic acid aqueous solution, and the resulting mixture was extracted with chloroform. The chloroform layer was dried over anhydrous sodium sulfate, and concentrated under reduced pressure. The obtained crude product was dissolved in 1 ml of methylene chloride, and 0.009 ml (0.25 mmol) of acetic anhydride and 12 mg (0.098 mmol) of dimethylaminopyridine were added thereto at 0° C. The mixture was stirred for 3 hours. To the reaction mixture was added a 0.2M phosphate buffer of pH 7, and the resulting mixture was extracted with chloroform. The chloroform layer was washed with a saturated aqueous solution of sodium chloride, dried over anhydrous sodium sulfate, and concentrated under reduced pressure. The obtained crude product was purified by silica-gel column chromatography (20 ml of silica gel, chloroform:methanol=100:1) to give 16 mg of Compound 14 (yield: 95%).

The physicochemical properties of Compound 14 are as follows.

$^1$H-NMR (270 MHz, CDCl$_3$) δ (ppm); 8.43 (1H, br), 8.31 (1H, br), 7.80 (1H, d, J=15.6Hz), 7.57 (2H, d, J=8.6Hz), 6.94 (2H, d, J=8.6Hz), 6.79 (2H, d, J=15.5Hz), 4.57 (1H, m), 4.48 (1H, br d, J=10.3Hz), 4.31 (1H, dd, J=9.5, 9.5Hz), 3.97 (3H, s), 3.86 (3H, s), 3.80 (1H, dd, J=10.5, 2.3Hz), 3.24 (1H, dd, J=10.4, 10.4Hz), 2.71 (3H, s), 2.40 (3H, s)

IR (KBr) ν (cm$^{-1}$); 1701, 1691, 1637, 1602, 1490, 1458, 1203

FABMS (m/z); 543, 541 (M) $^+$

EXAMPLE 15

Synthesis of Compound 15

Acetonitrile (0.61 ml) and 5.4 μl of 48% hydrobromic acid were added to 10.0 mg (0.0239 mmol) of Compound D, and the mixture was stirred at room temperature for 40 minutes. The reaction mixture was concentrated under reduced pressure. The obtained crude product was dissolved in 0.61 ml of methylene chloride, and 6.4 μl (0.074 mmol) of methyl chlorotiolformate and 10.0 μl (0.072 mmol) of triethylamine were added thereto at −78° C. The mixture was stirred at −78° C. for 80 minutes. To the reaction mixture was added a saturated aqueous solution of sodium hydrogen carbonate, and the resulting mixture was extracted with chloroform. The chloroform layer was washed with a saturated aqueous solution of sodium chloride, dried over anhydrous sodium sulfate, and concentrated under reduced pressure. The obtained crude product was purified by thin-layer chromatography (chloroform:methanol=15:1) to give 11.5 mg of Compound 15 (yield: 84%).

The physicochemical properties of Compound 15 are as follows.

$^1$H-NMR (270 MHz, CDCl$_3$) δ (ppm); 8.80 (1H, s), 8.37 (1H, brs), 7.80 (1H, d, J=15.2Hz), 7.56 (2H, d, J=8.6Hz), 6.93 (2H, d, J=8.9Hz), 6.79 (1H, d, J=15.2Hz), 4.50–4.59 (1H, m), 4.47 (1H, d, J=10.6Hz), 4.30 (1H, dd, J=9.2, 9.2Hz), 3.95 (3H, s), 3.85 (3H, s), 3.79 (1H, dd, J=10.2, 3.4Hz), 3.22 (1H, dd, J=10.2, 10.2Hz), 2.68 (3H, s), 2.44 (3H, s)

FABMS (m/z); 575, 573 (M+H) $^+$

IR (KBr) ν (cm$^{-1}$); 1701, 1610, 1506, 1404, 1294, 1265, 1234, 1196, 1176, 1111

EXAMPLE 16

Synthesis of Compound 16

Acetonitrile (1.16 ml) and 10.8 μl of 48% hydrobromic acid were added to 20.0 mg (0.0478 mmol) of Compound D, and the mixture was stirred at room temperature for 50 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 0.75 ml of methylene chloride, and 0.30 ml of methylene chloride containing 17.7 mg (0.143 mmol) of nicotinic acid and 29.6 mg (0.143 mmol) of dicyclohexylcarbodiimide was added thereto at −20° C. The mixture was stirred for 5 minutes. Subsequently, to the mixture was added 17.5 mg (0.143 mmol) of 4-dimethylaminopyridine, and the mixture was stirred at −20° C. to room temperature for 18.5 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=30:1) to give 18.8 mg of Compound 16 (yield: 65%).

The physicochemical properties of Compound 16 are as follows.

$^1$H-NMR (270 MHz, CDCl$_3$) δ (ppm); 10.89 (1H, brs), 9.34 (1H, d, J=1.7Hz), 8.75 (1H, dd, J=5.0, 1.7Hz), 8.35 (1H, brs), 8.27 (1H, dt, J=7.9, 1.7Hz), 7.77 (1H, d, J=15.2Hz), 7.56 (2H, d, J=8.6Hz), 7.36 (1H, dd, J=7.9, 5.0Hz), 6.93 (2H, d, J=8.6Hz), 6.79 (1H, d, J=15.2Hz), 4.58–4.69 (1H, m), 4.49 (1H, d, J=10.6Hz), 4.33 (1H, dd, J=10.2, 8.9Hz), 3.98 (3H, s), 3.85 (4H, s), 3.27 (1H, dd, J=10.2, 9.9Hz), 2.73 (3H, s)

FABMS (m/z); 606, 604 (M+H) $^+$

IR (KBr) ν (cm$^{-1}$); 1747, 1697, 1649, 1595, 1512, 1408, 1294, 1265, 1217, 1173, 1093

EXAMPLE 17

Synthesis of Compound 17

Anhydrous ethyl acetate (1.59 ml) was added to 19.8 mg (0.0328 mmol) of Compound 16 obtained in Example 16, and 9.56 μl of 6.86N hydrogen chloride in ehtanol was added thereto. The mixture was stirred at room temperature for 3 hours. The reaction mixture was concentrated under reduced pressure to give 19.9 mg of Compound 17.

The physicochemical properties of Compound 17 are as follows.

$^1$H-NMR (270 MHz, DMSO-d$_6$) δ (ppm); 12.14 (1H, brs), 9.37 (1H, s), 8.96 (1H, brd, J=4.0Hz), 8.58 (1H, dt, J=7.9, 2.0Hz), 8.23 (1H, s), 7.75 (2H, d, J=8.6Hz), 7.71–7.74 (1H, m), 7.60 (1H, d, J=15.5Hz), 7.07 (1H, d, J=15.5Hz), 7.00 (2H, d, J=8.6Hz), 4.41–4.59 (3H, m), 3.86 (4H, s), 3.81 (3H, s), 2.64 (3H, s)

IR (KBr) ν (cm$^{-1}$); 1697, 1645, 1601, 1512, 1408, 1281, 1252, 1217, 1174, 1097

EXAMPLE 18

Synthesis of Compound 18

Acetonitrile (1.74 ml) and 41 μl of 48% hydrobromic acid were added to 30.0 mg (0.0717 mmol) of Compound D, and the mixture was stirred at room temperature for 2 hours. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.74 ml of methylene chloride, and 43.4 mg (0.215 mmol) of p-nitrophenyl chloroformate and 30 μl (0.215 mmol) of triethylamine were added thereto at −78° C. The mixture was stirred for 40 minutes. Subsequently, to the mixture was added 43 μl (0.359 mmol) of 1-amino-4-methylpiperazine, and the mixture was stirred at −78° C. to 0° C. for 24 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=9:1) to give 20.4 mg of Compound 18 (yield: 44%).

The physicochemical properties of Compound 18 are as follows.

$^1$H-NMR (270 MHz, CDCl$_3$) δ (ppm); 9.85 (1H, brs), 8.25 (1H, brs), 7.79 (1H, d, J=15.5Hz), 7.55 (2H, d, J=8.6Hz), 7.07 (1H, br), 6.92 (2H, d, J=8.6Hz), 6.78 (1H, d, J=15.2Hz), 4.46–4.56 (1H, m), 4.42 (1H, d, J=10.2Hz), 4.26 (1H, dd, J=9.9, 8.6Hz), 3.91 (3H, s), 3.85 (3H, s), 3.75 (1H, dd, J=9.9, 2.3Hz), 3.18 (1H, dd, J=9.9, 9.9Hz), 2.95 (4H, br), 2.56 (3H, s), 2.52 (4H, br), 2.25 (3H, s)

FABMS (m/z); 642, 640 (M+H) $^+$

IR (KBr) ν (cm$^{-1}$); 1741, 1697, 1650, 1512, 1433, 1410, 1252, 1215, 1173, 1090

EXAMPLE 19

Synthesis of Compound 19

Ethanol (0.86 ml) and 0.43 ml of methanol were added to 20.4 mg (0.0318 mmol) of Compound 18 obtained in Example 18, and 13.9 μl of 6.86N hydrogen chloride in ethanol was added thereto. The mixture was stirred at room temperature for 3 hours. The reaction mixture was concentrated under reduced pressure to give 20.9 mg of Compound 19.

The physicochemical properties of Compound 19 are as follows.

$^1$H-NMR (270 MHz, DMSO-$d_6$) δ (ppm); 12.12 (1H, brs), 10.20 (1H, br), 9.149 (1H, brs), 8.03 (1H, s), 7.75 (2H, d, J=8.3Hz), 7.59 (1H, d, J=15.2Hz), 7.06 (1H, d, J=15.2Hz), 7.00 (2H, d, J=8.6Hz), 4.41–4.55 (3H, br), 3.84 (3H, s), 3.81 (3H, s), 3.78 (1H, br), 3.11–3.20 (7H, m), 2.79 (3H, s), 2.65 (3H, s)

IR (KBr) ν (cm$^{-1}$); 1749, 1697, 1647, 1512, 1437, 1414, 1250, 1219, 1188, 1093

EXAMPLE 20

Synthesis of Compound 20

Acetonitrile (1.74 ml) and 40.6 μl of 48% hydrobromic acid were added to 30.0 mg (0.0717 mmol) of Compound D, and the mixture was stirred at room temperature for 40 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.74 ml of methylene chloride, and 43.4 mg (0.215 mmol) of p-nitrophenyl chloroformate and 30 μl (0.215 mmol) of triethylamine were added thereto at –78° C. The mixture was stirred for 35 minutes. Subsequently, to the mixture was added 34.6 μl (0.359 mmol) of 4-aminomorpholine, and the mixture was stirred at –78° C. to room temperature for 23 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=9:1) to give 25.9 mg of Compound 20 (yield: 58%).

The physicochemical properties of Compound 20 are as follows.

$^1$H-NMR (270 MHz, CDCl$_3$) δ (ppm); 9.96 (1H, brs), 8.25 (1H, s), 7.81 (1H, d, J=15.2Hz), 7.54 (2H, d, J=8.9Hz), 7.42 (1H, brs), 6.91 (2H, d, J=8.9Hz), 6.77 (1H, d, J=15.2Hz), 4.42–4.56 (1H, m), 4.40 (1H, d, J=10.2Hz), 4.26 (1H, dd, J=9.2, 9.2Hz), 3.89 (3H, s), 3.84 (3H, s), 3.75 (1H, brd, J=8.3Hz), 3.65 (4H, br), 3.22 (1H, dd, J=9.6, 9.2Hz), 2.84 (4H, br), 2.52 (3H, s)

FABMS (m/z); 629, 627 (M+H) $^+$

IR (KBr) ν (cm$^{-1}$); 1697, 1647, 1603, 1512, 1435, 1414, 1252, 1215, 1111, 1090

EXAMPLE 21

Synthesis of Compound 21

Acetonitrile (1.45 ml) and 34 μl of 48% hydrobromic acid were added to 25.0 mg (0.0597 mmol) of Compound D, and the mixture was stirred at room temperature for 50 minutes. To the reaction mixture was then added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.31 ml of methylene chloride, and 24.9 mg (0.179 mmol) of 3-aminopyrazine-2-carboxylic acid and 37 mg (0.179 mmol) of dicyclohexylcarbodiimide were added thereto at –20° C. The mixture was stirred for 5 minutes. Subsequently, to the mixture was added 21.9 mg (0.179 mmol) of 4-dimethylaminopyridine, and the mixture was stirred at –20° C. to room temperature for 18.5 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=20:1) to give 24.1 mg of Compound 21 (yield: 64%).

The physicochemical properties of Compound 21 are as follows.

$^1$H-NMR (270 MHz, CDCl$_3$+CD$_3$OD) δ (ppm); 8.54 (1H, s), 8.29 ( 1H, d, J=2.0Hz ), 7.92 ( 1H, d, J=2.0Hz ), 7.73 ( 1H, d, J=15.5Hz), 7.53 (2H, d, J=8.6Hz), 6.89 (2H, d, J=8.9Hz), 6.76 (1H, d, J=14.8Hz), 4.48–4.59 (1H, m), 4.44 (1H, d, J=10.2Hz), 4.29 (1H, dd, J=9.9, 8.6Hz), 3.91 (3H, s), 3.81 (3H, s), 3.79 (1H, dd, J=8.6, 2.0Hz), 3.21 (1H, dd, J=10.2, 9.9Hz), 2.65 (3H, s)

FABMS (m/z); 622, 620 (M+H) $^+$

IR (KBr) ν (cm$^{-1}$); 1716, 1697, 1647, 1597, 1512, 1408, 1296, 1248, 1174, 1092

EXAMPLE 22

Synthesis of Compound 22

Acetonitrile (1.45 ml) and 34 μl of 48% hydrobromic acid were added to 25.0 mg (0.0597 mmol) of Compound D, and the mixture was stirred at room temperature for 60 minutes. To the reaction mixture was then added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.45 ml of methylene chloride, and 27 mg (0.179 mmol) of 3,4-diaminobenzoic acid and 37 mg (0.179 mmol) of dicyclohexylcarbodiimide were added thereto at –20° C. The mixture was stirred for 10 minutes. Subsequently, to the mixture was added 21.9 mg (0.179 mmol) of 4-dimethylaminopyridine, and the mixture was stirred at –20° C. to room temperature for 16 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=9:1) to give 13.7 mg of Compound 22 (yield: 36%).

The physicochemical properties of Compound 22 are as follows.

$^1$H-NMR (270 MHz, DMSO-$d_6$) δ (ppm); 12.06 (1H, brs), 8.07 (1H, brs), 7.75 (2H, d, J=8.6Hz), 7.59 (1H, d, J=15.5Hz), 7.37 (1H, s), 7.35 (1H, dd, J=8.2, 2.0Hz), 7.06 (1H, d, J=15.5Hz), 6.99 (2H, d, J=8.6Hz), 6.63 (1H, d, J=7.9Hz), 5.51 (2H, brs), 4.82 (2H, br), 4.39–4.57 (3H, m), 3.85 (3H, s), 3.83 (1H, brd, J=11.2Hz), 3.81 (3H, s), 3.45 (1H, dd, J=8.9, 8.9Hz), 2.62 (3H, s)

FABMS (m/z); 635, 633 (M+H)$^+$

IR (KBr) ν (cm$^{-1}$); 1701, 1693, 1645, 1593, 1512, 1410, 1306, 1250, 1205, 1092

EXAMPLE 23

Synthesis of Compound 23

Acetonitrile (1.45 ml) and 33.8 μl of 48% hydrobromic acid were added to 25.0 mg (0.0597 mmol) of Compound D, and the mixture was stirred at room temperature for 50 minutes. To the reaction mixture was further added 13.5 μl of 48% hydrobromic acid, and the mixture was stirred for 20 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 0.94 ml of methylene chloride, and 0.37 ml of methylene chloride containing 29.6 mg (0.179 mmol) of 4-dimethylaminobenzoic acid and 37 mg (0.179 mmol) of dicyclohexylcarbodiimide was added thereto at –20° C. The mixture was stirred for 5 minutes. Subsequently, to the mixture was added 21.9 mg (0.179 mmol) of 4-dimethylaminopyridine, and the mixture was stirred at –20° C. to room temperature for 18 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=80:1) to give 22.3 mg of Compound 23 (yield: 58%).

The physicochemical properties of Compound 23 are as follows.

$^1$H-NMR (270 MHz, CDCl$_3$) δ (ppm); 9.44 (1H, brs), 8.28 (1H, brs), 7.92 (2H, d, J=8.9Hz), 7.75 (1H, d, J=15.2Hz), 7.54 (2H, d, J=8.6Hz), 6.92 (2H, d, J=8.2Hz), 6.77 (1H, d, J=15.5Hz), 6.51 (2H, d, J=8.6Hz), 4.47–4.58 (1H, m), 4.43 (1H, d, J=10.2Hz), 4.25 (1H, dd, J=9.2, 8.2Hz), 3.94 (3H, s), 3.84 (3H, s), 3.82 (1H, brd, J=10.6Hz ), 3.19 (1H, dd, J=10.2, 9.9Hz ), 3.01 (6H, s), 2.50 (3H, s)

FABMS (m/z); 648, 646 (M+H)$^+$

IR (KBr) ν (cm$^{-1}$); 1697, 1647, 1603, 1512, 1406, 1267, 1174, 1155, 1088

EXAMPLE 24

Synthesis of Compound 24

Acetonitrile (2.32 ml) and 54.1 μl of 48% hydrobromic acid were added to 40.0 mg (0.0956 mmol) of Compound D, and the mixture was stirred at room temperature for 40 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 2.32 ml of methylene chloride, and 47.4 mg (0.287 mmol) of 3-dimethylaminobenzoic acid and 59.2 mg (0.287 mmol) of dicyclohexylcarbodiimide were added thereto at –20° C. The mixture was stirred for 5 minutes. Subsequently, to the mixture was added 35 mg (0.287 mmol) of 4-dimethylaminopyridine, and the mixture was stirred at –20° C. to room temperature for 17.5 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform) to give 43.8 mg of a crude product. Then, the crude product was purified by high-performance preparative liquid chromatography (acetonitrile:water=90:10) to give 31.6 mg of Compound 24 (yield: 51%).

The physicochemical properties of Compound 24 are as follows.

$^1$H-NMR (270 MHz, CDCl$_3$) δ (ppm); 9.57 (1H, brs), 8.30 (1H, brs), 7.73 (1H, d, J=15.2Hz), 7.53 (2H, d, J=8.6Hz), 7.42 (1H, d, J=7.9Hz), 7.34 (1H, brs), 7.18 (1H, dd, J=7.9, 7.9Hz), 6.92 (2H, d, J=8.6Hz), 6.83 (1H, dd, J=7.9, 2.6Hz), 6.72 (1H, d, J=15.2Hz), 4.45–4.58 (1H, m), 4.40 (1H, d, J=10.2Hz), 4.25 (1H, dd, J=9.2, 8.2Hz), 3.95 (3H, s), 3.84 (3H, s), 3.80 (1H, dd, J=9.6, 2.0Hz), 3.18 (1H, dd, J=10.2, 9.9Hz), 2.87 (6H, s), 2.56 (3H, s)

FABMS (m/z); 648, 646 (M+H)$^+$

IR (KBr) ν (cm$^{-1}$); 1734, 1697, 1653, 1603, 1512, 1458, 1406, 1250, 1173, 1093

EXAMPLE 25

Synthesis of Compound 25

Acetonitrile (2.32 ml) and 54.1 μl of 48% hydrobromic acid were added to 40.0 mg (0.0956 mmol) of Compound D, and the mixture was stirred at room temperature for 40 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 2.32 ml of methylene chloride, and 55.4 mg (0.287 mmol) of 4-diethylaminobenzoic acid and 59.2 mg (0.287 mmol) of dicyclohexylcarbodiimide were added thereto at –20° C. The mixture was stirred for 5 minutes. Subsequently, to the mixture was added 35 mg (0.287 mmol) of 4-dimethylaminopyridine, and the mixture was stirred at –20° C. to room temperature for 21.5 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by column chromatography (chloroform) to give 65.3 mg of a crude product. Then, the crude product was purified by thin-layer chromatography (chloroform:methanol=80:1) to give 43.4 mg of Compound 25 (yield: 67%).

The physicochemical properties of Compound 25 are as follows.

¹H-NMR (270 MHz, CDCl₃) δ (ppm); 8.97 (1H, brs), 8.33 (1H, brs), 7.99 (2H, d, J=9.2Hz), 7.78 (1H, d, J=15.2Hz), 7.56 (2H, d, J=8.6Hz), 6.93 (2H, d, J=8.9Hz), 6.80 (1H, d, J=15.2Hz), 6.61 (2H, d, J=8.9Hz), 4.50–4.63 (1H, m), 4.46 (1H, d, J=10.6Hz), 4.29 (1H, dd, J=9.9, 8.3Hz), 3.96 (3H, s), 3.85 (3H, s), 3.83 (1H, dd, J=11.6, 2.2Hz), 3.43 (4H, q, J=6.9Hz), 3.22 (1H, dd, J=10.2, 9.9Hz), 2.59 (3H, s), 1.21 (6H, t, J=6.9Hz)

FABMS (m/z); 676, 674 (M+H) ⁺

IR (KBr) ν (cm⁻¹); 1716, 1697, 1653, 1603, 1512, 1408, 1261, 1182, 1155, 1090

EXAMPLE 26

Synthesis of Compound 26

Acetonitrile (1.74 ml) and 40.6 μl of 48% hydrobromic acid were added to 30.0 mg (0.0717 mmol) of Compound D, and the mixture was stirred at room temperature for 40 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 2.32 ml of methylene chloride, and 40.3 mg (0.215 mmol) of 4-(1H-pyrrol-1-yl)benzoic acid and 44.4 mg (0.215 mmol) of dicyclohexylcarbodiimide were added thereto at −20° C. The mixture was stirred for 5 minutes. Subsequently, to the mixture was added 26.3 mg (0.215 mmol) of 4-dimethylaminopyridine, and the mixture was stirred at −20° C. to room temperature for 17 hours and 15 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by column chromatography (chloroform) to give 29.3 mg of a crude product. Then, the crude product was purified by high-performance preparative liquid chromatography (acetonitrile:water= 90:10) to give 20.2 mg of Compound 26 (yield: 42%).

The physicochemical properties of Compound 26 are as follows.

¹H-NMR (270 MHz, CDCl₃) δ (ppm); 10.24 (1H, brs), 8.28 (1H, s), 8.03 (2H, d, J=7.9Hz), 7.71 (1H, d, J=15.2Hz), 7.52 (2H, d, J=8.6Hz), 7.13 (2H, d, J=7.3Hz), 6.93 (2H, brs), 6.91 (2H, d, J=8.2Hz), 6.67 (1H, d, J=15.2Hz), 6.29 (2H, brs), 4.20–4.48 (1H, br), 4.29 (1H, d, J=10.9Hz), 3.99–4.15 (1H, m), 3.92 (3H, s), 3.84 (3H, s), 3.67 (1H, brd, J=9.2Hz), 3.02 (1H, dd, J=10.2, 9.6Hz), 2.56 (3H, s)

FABMS (m/z); 670, 668 (M+H) ⁺

IR (KBr) ν (cm⁻¹); 1699, 1653, 1606, 1512, 1473, 1408, 1335, 1261, 1182, 1092

EXAMPLE 27

Synthesis of Compound 27

Acetonitrile (1.16 ml) and 27 μl of 48% hydrobromic acid were added to 20.0 mg (0.0478 mmol) of Compound D, and the mixture was stirred at room temperature for 40 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.16 ml of methylene chloride, and 33.6 mg (0.143 mmol) of 4-(4-methylpiperazinylmethyl)benzoic acid and 29.6 mg (0.143 mmol) of dicyclohexylcarbodiimide were added thereto at −20° C. The mixture was stirred for 5 minutes. Subsequently, to the mixture was added 17.5 mg (0.143 mmol) of 4-dimethylaminopyridine, and the mixture was stirred at −20° C. to room temperature for 21 hours and 15 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=9:1) to give 20.9 mg of Compound 27 (yield: 61%).

The physicochemical properties of Compound 27 are as follows.

¹H-NMR (270 MHz, CDCl₃) δ (ppm); 9.16–9.28 (1H, br), 8.33 (1H, brs), 8.08 (2H, d, J=7.9Hz), 7.75 (1H, d, J=15.2Hz), 7.54 (2H, d, J=8.3Hz), 7.40 (2H, d, J=7.9Hz), 6.92 (2H, d, J=8.6Hz), 6.76 (1H, d, J=15.5Hz), 4.51–4.61 (1H, m), 4.44 (1H, d, J=9.9Hz), 4.28 (1H, dd, J=8.9, 7.6Hz), 3.95 (3H, s), 3.84 (3H, s), 3.80 (1H, brd, J=8.5Hz), 3.55 (2H, s), 3.21 (1H, dd, J=10.2, 9.9Hz), 2.61 (3H, s), 2.49 (8H, brs), 2.31 (3H, s)

FABMS (m/z); 717, 715 (M+H) ⁺

IR (KBr) ν (cm⁻¹); 1697, 1653, 1647, 1601, 1512, 1408, 1250, 1217, 1173, 1090

EXAMPLE 28

Synthesis of Compound 28

Anhydrous ethyl acetate (1.81 ml) was added to 12.7 mg (0.0177 mmol) of Compound 27 obtained in Example 27, and 172 mg of 5% hydrobromic acid in methanol was added thereto. The mixture was stirred at room temperature for 1.5 hours. The reaction mixture was concentrated under reduced pressure to give 16.0 mg of Compound 28.

The physicochemical properties of Compound 28 are as follows.

¹H-NMR (270 MHz, DMSO-d₆) δ (ppm); 12.14 (1H, s), 9.40–9.80 (1H, br), 8.24 (2H, d, J=8.3Hz), 8.17 (1H, s), 7.76 (2H, d, J=8.6Hz), 7.67 (2H, d, J=7.3Hz), 7.59 (1H, d, J=15.5Hz), 7.08 (1H, d, J=15.2Hz), 7.00 (2H, d, J=8.6Hz), 4.44–4.54 (3H, m), 3.86 (3H, s), 3.81 (3H, s), 3.49 (2H, d, J=6.6Hz), 3.06–3.21 (3H, m), 2.84 (3H, s), 2.63 (3H, s)

IR (KBr) ν (cm⁻¹); 1734, 1697, 1653, 1601, 1512, 1437, 1412, 1252, 1217, 1174, 1093

EXAMPLE 29

Synthesis of Compound 29

Acetonitrile (1.74 ml) and 41 μl of 48% hydrobromic acid were added to 30.0 mg (0.0717 mmol) of Compound D, and the mixture was stirred at room temperature for 1 hour. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.74 ml of methylene chloride, and 43.4 mg (0.215 mmol) of p-nitrophenyl chloroformate and 30 μl (0.215 mmol) of triethylamine were added thereto at −78° C. The mixture was stirred for 1.5 hours. Subsequently, to the mixture was further added 14.5 mg (0.0717 mmol) of p-nitrophenyl chloroformate, and the mixture was stirred for 30 minutes. Then, 27.2 μl (0.359 mmol) of 1,1-dimethylhydrazine was added thereto, and the mixture was stirred at −78° to −20° C. for 24 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=20:1) to give 18.9 mg of Compound 29 (yield: 45%).

The physicochemical properties of Compound 29 are as follows.

$^1$H-NMR (270 MHz, CDCl$_3$) δ (ppm); 9.76 (1H, brs), 8.23 (1H, brs), 7.80 (1H, d, J=15.5Hz), 7.56 (2H, d, J=8.6Hz), 7.03 (1H, brs), 6.92 (2H, d, J=8.9Hz), 6.79 (1H, d, J=15.2Hz), 4.43–4.51 (1H, m), 4.40 (1H, d, J=10.9Hz), 4.23 (1H, dd, J=9.6, 9.2Hz), 3.89 (3H, s), 3.84 (3H, s), 3.71 (1H, dd, J=7.3, 2.3Hz), 3.15 (1H, dd, J=9.6, 9.6Hz), 2.65 (6H, s), 2.53 (3H, s)

FABMS (m/z); 587, 585 (M+H) $^+$

IR (KBr) ν (cm$^{-1}$); 2953, 1695, 1647, 1603, 1512, 1421, 1410, 1250, 1215, 1173, 1093

EXAMPLE 30

Synthesis of Compound 30

Acetonitrile (0.87 ml) and 20.3 μl of 48% hydrobromic acid were added to 15.0 mg (0.0358 mmol) of Compound D, and the mixture was stirred at room temperature for 50 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 0.87 ml of methylene chloride, and 21.6 mg (0.107 mmol) of p-nitrophenyl chloroformate and 15 μl (0.107 mmol) of triethylamine were added thereto at −78° C. The mixture was stirred for 40 minutes. Subsequently, to the mixture was added 9.5 μl (0.179 mmol) of 1-methylhydrazine, and the mixture was stirred at −78° C. to 0° C. for 100 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=12:1) to give 14.6 mg of Compound 30 (yield: 71%).

The physicochemical properties of Compound 30 are as follows.

$^1$H-NMR (270 MHz, CDCl$_3$) δ (ppm); 9.81–10.21 (1H, br), 8.24 (1H, brs), 7.81 (1H, d, J=15.2Hz), 7.57 (2H, d, J=8.3Hz), 6.93 (2H, d, J=8.6Hz), 6.82 (1H, d, J=15.5Hz), 4.47–4.55 (1H, br), 4.46 (1H, d, J=10.2Hz), 4.33 (1H, dd, J=9.2, 8.9Hz), 3.94 (3H, s), 3.85 (3H, s), 3.77 (1H, dd, J=9.4, 2.1Hz), 3.29 (3H, brs), 3.19 (1H, dd, J=9.9, 9.9Hz), 2.32 (3H, s)

FABMS (m/z); 573, 571 (M+H) $^+$

IR (KBr) ν (cm$^{-1}$); 1697, 1647, 1599, 1512, 1433, 1410, 1248, 1217, 1173, 1111

EXAMPLE 31

Synthesis of Compound 31

Acetonitrile (3.78 ml) and 89.4 μl of 48% hydrobromic acid were added to 66.1 mg (0.158 mmol) of Compound D, and the mixture was stirred at room temperature for 50 minutes. To the reaction mixture was added a 1N hydrobromic acid aqueous solution, and the resulting mixture was extracted with chloroform. The chloroform layer was washed with an aqueous solution of sodium chloride, dried over anhydrous sodium sulfate, and concentrated under reduced pressure. The obtained crude product was dissolved in 3.0 ml of methylene chloride, and 95.5 mg (0.474 mmol) of p-nitrophenyl chloroformate and 66 μl (0.474 mmol) of triethylamine were added thereto at −78° C., and the mixture was stirred for 45 minutes. To the mixture was added 0.78 ml of a dichloromethane solution containing 101 mg (0.553 mmol) of 1-amino-4-piperidinopiperidine, and the mixture was stirred at 0° C. to room temperature for 23.5 hours. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol:triethylamine=9:1:0.2) to give 48.5 mg of Compound 31 (yield: 43%).

The physicochemical properties of Compound 31 are as follows.

$^1$H-NMR (270 MHz, CDCl$_3$) δ (ppm); 9.85 (1H, brs), 8.27 (1H, brs), 7.78 (1H, d, J=15.2Hz), 7.55 (2H, d, J=8.6Hz), 7.01 (1H, br), 6.92 (2H, d, J=8.9Hz), 6.79 (1H, d, J=14.9Hz), 4.48–4.59 (1H, m), 4.43 (1H, d, J=9.9Hz), 4.28 (1H, dd, J=9.6, 8.6Hz), 3.92 (3H, s), 3.85 (3H, s), 3.78 (1H, dd, J=9.4, 2.5Hz), 3.29 (2H, br), 3.20 (1H, dd, J=10.2, 10.2Hz), 2.64 (3H, s), 2.59 (9H, br), 1.84 (3H, br), 1.65 (3H, br), 1.45 (2H, br)

FABMS (m/z); 710, 708 (M+H) $^+$

IR (KBr) ν (cm$^-$); 1697, 1645, 1601, 1512, 1433, 1410, 1252, 1215, 1173, 1107

EXAMPLE 32

Synthesis of Compound 32

Anhydrous ethyl acetate (2.5 ml) was added to 30.6 mg (0.0432 mmol) of Compound 31 obtained in Example 31, and 210 mg of 5% hydrobromic acid in methanol was added thereto. The mixture was stirred at −20° C. for 40 minutes. The reaction mixture was concentrated under reduced pressure to give 35.6 mg of Compound 32.

The physicochemical properties of Compound 32 are as follows.

$^1$H-NMR (270 MHz, DMSO-d$_6$) δ (ppm); 12.04 (1H, brs), 9.25 (1H, s), 9.00 (1H, br), 8.02 (1H, s), 7.75 (2H, d, J=8.6Hz), 7.59 (1H, d, J=15.2Hz), 7.06 (1H, d, J=15.2Hz), 7.00 (2H, d, J=8.9Hz), 4.36–4.53 (3H, m), 3.85 (3H, s), 3.82

(3H, s), 3.78 (1H, m), 3.17–3.27 (2H, m), 2.86–3.04 (1H, m), 2.69–2.79 (2H, m), 2.65 (3H, s), 1.99–2.07 (2H, br), 1.60–1.91 (9H, m), 1.34–1.49 (2H, m)

IR (KBr) ν (cm$^{-1}$); 1749, 1695, 1645, 1601, 1512, 1456, 1412, 1250, 1217, 1174

EXAMPLE 33

Synthesis of Compound 33

Acetonitrile (1.45 ml) and 33.8 μl of 48% hydrobromic acid were added to 25.0 mg (0.0597 mmol) of Compound D, and the mixture was stirred at room temperature for 1 hour. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.45 ml of methylene chloride, and 24.5 mg (0.185 mmol) of thiodiglycolic anhydride and 23.3 mg (0.191 mmol) of 4-dimethylaminopyridine were added thereto at 0° C. The mixture was stirred at 0° C. for 3 hours. To the reaction mixture was added a 0.01M phosphate buffer of pH 7 and a 1N hydrobromic acid aqueous solution, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol:acetic acid=4:1:0.1) to give 25.9 mg of Compound 33 (yield: 69%).

The physicochemical properties of Compound 33 are as follows.

$^1$H-NMR (270 MHz, CDCl$_3$) δ (ppm); 10.40 (1H, brs), 8.02 (1H, s), 7.66 (1H, d, J=15.2Hz), 7.49 (2H, d, J=8.3Hz), 6.88 (2H, d, J=8.3Hz), 6.63 (1H, d, J=15.5Hz), 4.36–4.46 (1H, m), 4.29 (1H, d, J=10.6Hz), 4.11 (H, dd, J=9.9, 9.2Hz), 3.89 (3H, s), 3.82 (3H, s), 3.64 (1H, dd, J=9.9, 2.3Hz), 3.59 (2H, s), 3.40 (1H, d, J=14.8Hz), 3.33 (1H, d, J=14.8Hz), 3.07 (1H, dd, J=10.2, 9.9Hz), 2.50 (3H, s)

FABMS (m/z); 633, 631 (M+H)$^+$

IR (KBr) ν (cm$^{-1}$); 1697, 1637, 1603, 1512, 1437, 1416, 1252, 1219, 1174, 1105

EXAMPLE 34

Synthesis of Compound 34

Acetonitrile (1.74 ml) and 40.6 μl of 48% hydrobromic acid were added to 30.0 mg (0.0717 mmol) of Compound D, and the mixture was stirred at room temperature for 60 minutes. To the reaction mixture was added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.74 ml of methylene chloride, and 54.1 mg (0.215 mmol) of 4-(tert-butoxycarbonylaminomethyl) benzoic acid and 44.4 mg (0.215 mmol) of dicyclohexylcarbodiimide were added thereto at -20° C. The mixture was stirred for 5 minutes. Subsequently, to the mixture was added 26.3 mg (0.215 mmol) of 4-dimethylaminopyridine, and the mixture was stirred at -20° C. to room temperature for 5.5 hours. To the reaction mixture was added a 0.01M phosphate buffer of pH 7, and the resulting mixture was extracted with chloroform. The chloroform layer was washed with a saturated aqueous solution of sodium chloride, dried over anhydrous sodium sulfate, and concentrated under reduced pressure. The obtained crude product was purified by column chromatography (chloroform and methanol:30:1) to give 44.3 mg of a crude product. Subsequently, the crude product was purified by high-performance liquid chromatography (acetonitrile:water= 80:20) to give 28.5 mg of Compound 34 (yield: 54%).

The physicochemical properties of Compound 34 are as follows.

$^1$H-NMR (270 MHz, CDCl$_3$) δ (ppm); 9.44–9.76 (1H, brs), 8.30 (1H, brs), 8.00 (2H, d, J=7.3Hz), 7.75 (1H, d, J=15.2Hz), 7.55 (2H, d, J=8.6Hz), 7.22 (2H, d, J=7.3Hz), 6.92 (2H, d, J=8.9Hz), 6.76 (1H, d, J=15.2Hz), 5.25 (1H, brs), 4.47–4.59 (1H, m), 4.43 (1H, d, J=10.9Hz), 4.21–4.38 (3H, m), 3.94 (3H, s), 3.84 (3H, s), 3.81 (1H, brd, J=10.9Hz), 3.20 (1H, dd, J=10.2, 10.2Hz), 1.45 (9H, s)

FABMS (m/z); 734, 732 (M+H)$^+$

IR (KBr) ν (cm$^{-1}$); 1705, 1695, 1645, 1512, 1410, 1261, 1217, 1173, 1090, 1016

EXAMPLE 35

Synthesis of Compound 35

1,2-Dichloromethane (2.0 ml) and 1.445 g (0.893 mmol) of 5% hydrobromic acid in methanol were added to 65.4 mg (0.0717 mmol) of the crude product obtained in Example 34, and the mixture was stirred at 60° C. for 5 hours and 45 minutes. A saturated aqueous solution of sodium hydrogen carbonate was added to the reaction mixture, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform and methanol:4:1) to obtain 84.5 mg of a crude product. Subsequently, the crude product was purified by column chromatography (chloroform:methanol= 10:1) to give 15.1 mg of Compound 35 (yield: 33%).

The physicochemical properties of Compound 35 are as follows.

$^1$H-NMR (270 MHz, CDCl$_3$+CD$_3$OD) δ (ppm); 8.25 (1H, brs), 8.13 (2H, d, J=7.9Hz), 7.70 (1H, d, J=15.2Hz), 7.51 (2H, d, J=8.6Hz), 7.37 (2H, d, J=8.2Hz), 6.88 (2H, d, J=8.6Hz), 6.75 (1H, d, J=15.5Hz), 4.47–4.58 (1H, m), 4.42 (1H, d, J=10.6Hz), 4.26 (1H, dd, J=9.6, 8.9Hz), 3.91 (3H, s), 3.89 (2H, s), 3.81 (3H, s), 3.78 (1H, brd, J=8.4Hz), 3.19 (1H, dd, J=9.9, 9.9Hz), 2.61 (3H, s)

FABMS (m/z); 634, 632 (M+H)$^+$

IR (KBr) ν (cm$^{-1}$); 1732, 1695, 1647, 1601, 1512, 1410, 1259, 1219, 1174, 1092

EXAMPLE 36

Synthesis of Compound 36

Anhydrous ethyl acetate (1.17 ml) was added to 11.1 mg (0.0175 mmol) of compound 35 obtained in Example 35, and 85 mg of 5% hydrobromic acid in methanol was added thereto. The mixture was stirred at room temperature for 1 hour. The reaction mixture was concentrated under reduced pressure to give 14.6 mg of Compound 36.

The physicochemical properties of Compound 36 are as follows.

¹H-NMR (270 MHz, DMSO-d₆) δ (ppm); 12.15 (1H, brs), 8.32 (2H, br), 8.27 (2H, d, J=8.2Hz), 8.18 (1H, brs), 7.75 (2H, d, J=8.3Hz), 7.72 (2H, d, J=7.6Hz), 7.58 (1H, d, J=15.5Hz), 7.08 (1H, d, J=15.2Hz), 7.00 (2H, d, J=8.6Hz), 4.50–4.60 (1H, m), 4.41–4.48 (2H, br), 4.21–4.23 (2H, m), 3.86 (3H, s), 3.83 (1H, brd), 3.81 (3H, s), 2.63 (3H, s)

IR (KBr) ν (cm⁻¹); 1734, 1697, 1635, 1601, 1514, 1437, 1417, 1259, 1174, 1093

EXAMPLE 37

Synthesis of Compound 37

Anhydrous ethyl acetate (1.25 ml) was added to 19.6 mg (0.0306 mmol) of compound 18 obtained in Example 18, and 149 mg of 5% hydrobromic acid in methanol was added thereto. The mixture was stirred at 0° C. for 1 hour. The reaction mixture was concentrated under reduced pressure to give 23 mg of Compound 37.

The physicochemical properties of Compound 37 are as follows.

¹H-NMR (270 MHz, DMSO-d₆) δ (ppm); 12.07 (1H, brs), 9.49 (2H, brs), 8.04 (1H, brs), 7.76 (2H, d, J=8.3Hz), 7.59 (1H, d, J=15.2Hz), 7.07 (1H, d, J=15.5Hz), 7.00 (2H, d, J=7.3Hz), 4.38–4.56 (3H, br), 3.85 (3H, s), 3.82 (3H, s), 3.77 (1H, br), 3.02–3.30 (5H, m), 2.82 (3H, s), 2.66 (3H, s)

IR (KBr) ν (cm⁻¹); 1697, 1647, 1601, 1512, 1437, 1412, 1250, 1217, 1174, 1093

EXAMPLE 38

Synthesis of Compound 38

Acetonitrile (1.2 ml) and 27 µl of 48% hydrobromic acid were added to 20.0 mg (0.0478 mmol) of Compound D, and the mixture was stirred at room temperature for 40 minutes. To the reaction mixture was then added a 1N hydrobromic acid aqueous solution, and the resulting mixture was extracted with chloroform. The chloroform layer was washed with a saturated aqueous solution of sodium chloride, dried over anhydrous sodium sulfate, and concentrated under reduced pressure. The obtained crude product was dissolved in 1.1 ml of methylene chloride, and 28.9 mg (0.143 mmol) of p-nitrophenyl chloroformate and 20 µl (0.143 mmol) of triethylamine were added thereto at –78° C. The mixture was stirred for 45 minutes. Then, to the mixture was added a solution of 31.8 mg (0.239 mmol) of 1,2-dimethylhydrazine dihydrochloride and 67 µl (0.478 mmol) of triethylamine in 0.31 ml of chloroform. The mixture was stirred at –20° C. for 2 hours and 25 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, dried over anhydrous sodium sulfate, and concentrated under reduced pressure. The obtained crude product was purified by thin-layer chromatography (chloroform:methanol=20:1) to give 12.9 mg of Compound 38 (yield: 46%).

The physicochemical properties of Compound 38 are as follows.

¹H-NMR (270 MHz, CDCl₃) δ (ppm); 9.65 (1H, brs), 9.39 (1H, brs), 8.24 (1H, s), 7.80 (1H, d, J=15.2Hz), 7.57 (2H, d, J=8.9Hz), 6.94 (2H, d, J=8.9Hz), 6.81 (1H, d, J=15.5Hz), 4.50–4.57 (1H, m), 4.46 (1H, d, J=10.2Hz), 4.31 (1H, dd, J=9.6, 8.9Hz), 3.94 (3H, s), 3.86 (3H, s), 3.78 (1H, dd, J=9.7, 2.5Hz), 3.27 (3H, brs), 3.20 (1H, dd, J=10.2, 9.9Hz), 2.71 (3H, brs), 2.44 (3H, brs)

FABMS (m/z); 587, 585 (M+H)⁺

IR (KBr) ν (cm⁻¹); 1716, 1697, 1686, 1647, 1601, 1512, 1410, 1252, 1219, 1173, 1159, 1109

EXAMPLE 39

Synthesis of Compound 39

Acetonitrile (1.58 ml) and 348 mg of 5% hydrobromic acid in methanol were added to 30.0 mg (0.0717 mmol) of Compound D, and the mixture was stirred at room temperature for 30 minutes. The reaction mixture was concentrated under reduced pressure. The obtained crude product was dissolved in 1.58 ml of methylene chloride, and 49.7 mg (0.215 mmol) of 2-(4-methylpiperazinyl)acetic acid dihydrochloride and 41.1 mg (0.215 mmol) of N-ethyl-N'-3-dimethylaminopropylcarbodiimide hydrochloride were added thereto at –20° C. The mixture was stirred for 5 minutes. To the reaction mixture was then added 52.6 mg (0.430 mmol) of 4-dimethylaminopyridine, and the mixture was stirred at –20° C. for 4 hours and 10 minutes. To the reaction mixture was added a saturated aqueous solution of sodium hydrogen carbonate, and the resulting mixture was extracted with chloroform. The chloroform layer was washed with a saturated aqueous solution of sodium hydrogen carbonate and with a saturated aqueous solution of sodium chloride, and dried over anhydrous sodium sulfate. Trifluoroacetic acid was then added thereto, and the mixture was concentrated under reduced pressure. To the obtained crude product were added 2.00 ml of anhydrous ethyl acetate and 355 mg of 5% hydrobromic acid in methanol, and the mixture was stirred at –20° C. for 1 hour. The precipitated crystals were collected by filtration, washed with ethyl acetate, and dried under reduced pressure to give 14.4 mg of Compound 39 (yield 25%).

The physicochemical properties of Compound 39 are as follows.

¹H-NMR (270 MHz, DMSO-d₆) δ (ppm); 12.06 (1H, s), 9.45 (1H, brs), 8.10 (1H, s), 7.75 (2H, d, J=8.6Hz), 7.59 (1H, d, J=15.5Hz), 7.70 (1H, d, J=15.2Hz), 7.00 (2H, d, J=8.9Hz), 4.36–4.58 (3H, br), 3.89 (2H, s), 3.85 (3H, s), 3.81 (3H, s), 3.80 (1H, brd, J=9.9Hz), 3.38–3.50 (3H, m), 3.03–3.20 (4H, m), 2.82 (5H, br), 2.66 (3H, s)

IR (KBr) ν (cm⁻¹); 1647, 1637, 1601, 1512, 1458, 1437, 1410, 1250, 1207, 1174

EXAMPLE 40

Synthesis of Compound 40

Acetonitrile (1.58 ml) and 348 mg of 5% hydrobromic acid in methanol were added to 30.0 mg (0.0717 mmol) of Compound D, and the mixture was stirred at room temperature for 30 minutes. The reaction mixture was concentrated under reduced pressure. The obtained crude product was dissolved in 1.58 ml of methylene chloride, and 64.4 mg (0.215 mmol) of 2-(4-piperidinopiperidinyl)acetic acid dihydrochloride and 41.1 mg (0.215 mmol) of N-ethyl-N'-3-dimethylaminopropylcarbodiimide hydrochloride were added thereto at –20° C. The mixture was stirred for 5 minutes. Subsequently, 52.6 mg (0.430 mmol) of 4-dimethylaminopyridine was added to the mixture, and the mixture was stirred at −20° C. to room temperature for 7 hours. A saturated aqueous solution of sodium hydrogen carbonate was added to the reaction mixture, and the resulting mixture was extracted with chloroform. The chloroform layer was washed with a saturated aqueous solution of sodium hydrogen carbonate and with a saturated aqueous solution of sodium chloride, and dried over anhydrous sodium sulfate. Trifluoroacetic acid was added thereto, and the mixture was concentrated under reduced pressure. Anhydrous ethyl acetate (2.00 ml) and 580 mg of 5% hydrobromic acid in methanol were added to the obtained crude product, and the mixture was stirred at −20° C. for 1 hour. The precipitated crystals were collected by filtration, washed with ethyl acetate, and dried under reduced pressure to give 48.1 mg of Compound 40 (yield: 77%).

The physicochemical properties of Compound 40 are as follows.

$^1$H-NMR (270 MHz, DMSO-$d_6$) δ (ppm); 12.19 (1H, s), 9.38 (1H, brs), 8.20 (1H, s), 7.76 (2H, d, J=8.6Hz), 7.59 (1H, d, J=15.2Hz), 7.08 (1H, d, J=15.6Hz), 7.00 (2H, d, J=8.6Hz), 4.38–4.60 (3H, m), 4.41 (1H, br), 3.85 (3H, s), 3.82 (3H, s), 3.79 (1H, m), 3.37–3.73 (5H, m), 2.86–3.23 (4H, m), 2.68 (3H, s), 2.25 (2H, br), 1.64–2.16 (7H, m), 1.44 (1H, br)

IR (KBr) ν (cm$^{-1}$); 1695, 1686, 1645, 1601, 1512, 1437, 1410, 1250, 1176, 1109

REFERENCE EXAMPLE 1

Synthesis of Compound a

Compound E (705 mg, 1.03 mmol) was dissolved in 36 ml of tetrahydrofuran, and 1.55 ml of a 1M tetrahydrofuran solution of tetra-n-butylammonium fluoride was added thereto. The mixture was stirred at room temperature for 1 hour. Phosphate buffer (pH 7) was added to the reaction mixture, and the resulting mixture was extracted with ethyl acetate. The ethyl acetate layer was washed with a saturated aqueous solution of sodium chloride, dried over anhydrous sodium sulfate, and concentrated under reduced pressure. The obtained crude product was dissolved in 53 ml of N,N-dimethylformamide, and 11 ml of 70% perchloric acid and 21 ml of water were added thereto at 0° C. The mixture was stirred at 0° C. to room temperature for 2 hours. A saturated aqueous solution of sodium hydrogen carbonate was added to the reaction mixture, and the resulting mixture was extracted with ethyl acetate. The ethyl acetate layer was washed with a saturated aqueous solution of sodium chloride, dried over anhydrous sodium sulfate, and concentrated under reduced pressure. The obtained crude product was purified by silica-gel column chromatography (160 ml of silica gel, chloroform:methanol=30:1) to give 385 mg of Compound a (yield: 73%).

The physicochemical properties of Compound a are as follows.

$^1$H-NMR (400 MHz, DMSO-$d_6$) δ (ppm); 11.36 (1H, br s), 9.52 (1H, s), 7.82 (1H, br s), 6.97 (1H, d, J=2.2Hz), 6.87 (1H, s), 4.67 (1H, br d, J=9.8Hz), 4.47 (1H, dd, J=5.3, 5.3Hz), 4.39 (1H, dd, J=10.1, 8.4Hz), 4.18 (1H, m), 4.05 (3H, s), 3.89 (3H, s), 3.88 (3H, s), 3.86 (3H, s), 3.73 (1H, dd, J=10.5, 5.0Hz), 2.66 (3H, s)

IR (KBr) ν (cm$^{-1}$); 1595, 1490, 1442, 1320, 1223, 1161

SIMS (m/z); 510 (M) $^+$, 234

REFERENCE EXAMPLE 2

Synthesis of Compound b

Compound a (50 mg, 0.098 mmol) was dissolved in 3 ml of N,N-dimethylformamide, and 20 mg (0.14 mmol) of potassium carbonate and 22 ml (0.19 mmol) of benzyl bromide were added thereto. The mixture was stirred at room temperature for 48 hours. Phosphate buffer (pH 7) was added to the reaction mixture, and the resulting mixture was extracted with ethyl acetate. The ethyl acetate layer was washed with a saturated aqueous solution of sodium chloride, dried over anhydrous sodium sulfate, and concentrated under reduced pressure. The obtained crude product was purified by silica-gel column chromatography (20 ml of silica gel, chloroform:methanol=100:1) to give 40 mg of Compound b (yield: 68%).

The physicochemical properties of Compound b are as follows.

$^1$H-NMR (400 MHz, CDCl$_3$) δ (ppm); 9.39 (1H, br s), 8.63 (1H, br s), 8.18 (1H, s), 7.50–7.37 (5H, m), 6.99 (1H, d, J=2.3Hz), 6.86 (1H, s), 5.24 (2H, d, J=11.0Hz), 4.66 (1H, dd, J=10.1, 1.2Hz), 4.52 (1H, dd, J=10.0, 8.5Hz), 4.38 (1H, m), 4.07 (3H, s), 3.94 (3H, s), 3.91 (3H, s), 3.90 (3H, s), 3.85 (1H, dd, J=10.5, 4.7Hz), 3.58 (1H, dd, J=10.5, 6.5Hz), 2.68 (3H, s)

IR (KBr) ν (cm$^{-1}$); 1671, 1636, 1597, 1492, 1443, 1417, 1313, 1219, 1113

EIMS (m/z); 599 (M+1) $^+$, 234

REFERENCE EXAMPLE 3

Synthesis of Compound c

Compound a (100 mg, 0.195 mmol) was dissolved in 5 ml of N,N-dimethylformamide, and 41 mg (0.30 mmol) of potassium carbonate and 0.019 ml (0.31 mmol) of methyl iodide were added thereto. The mixture was stirred at room temperature for 24 hours. Then, 0.01M phosphate buffer (pH 7) was added to the reaction mixture, and the resulting mixture was extracted with ethyl acetate. The ethyl acetate layer was washed with a saturated aqueous solution of sodium chloride, dried over anhydrous sodium sulfate, and concentrated under reduced pressure. The obtained crude product was purified by silica-gel column chromatography (20 ml of silica gel, chloroform:methanol=80:1) to give 52 mg of Compound c (yield: 51%).

The physicochemical properties of Compound c are as follows.

$^1$H-NMR (400 MHz, CDCl$_3$) δ (ppm); 9.39 (1H, br s), 8.26 (1H, br s), 8.05 (1H, s), 6.99 (1H, d, J=2.3Hz), 6.86 (1H, s), 4.66 (1H, dd, J=10.2, 1.2Hz), 4.52 (1H, dd, J=10.1, 10.1Hz), 4.37 (1H, m), 4.07 (3H, s), 4.00 (3H, s), 3.94 (3H, s), 3.91 (3H, s), 3.90 (3H, s), 3.85 (1H, dd, J=10.4, 4.7Hz), 3.59 (1H, dd, J=10.5, 7.4Hz), 2.69 (3H, s)

IR (KBr) ν (cm$^{-1}$); 1670, 1634, 1521, 1446, 1411, 1313, 1221,

SIMS (m/z); 524 (M+H) $^+$, 234

INDUSTRIAL AVAILABILITY

The present invention relates to DC-89 derivatives. The compounds of the present invention exhibit excellent anti-tumor activity and are useful as anti-tumor agents.

We claim:
1. A DC-89 derivative represented by the formula

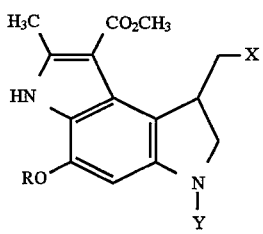

wherein X represents Cl or Br; R represents substituted or unsubstituted lower alkyl (wherein the substituted lower alkyl is substituted with 1 to 3 moieties selected from the group consisting of lower alkoxy, lower alkylthio optionally substituted with carboxy, carboxy, lower alkoxycarbonyl, benzyloxycarbonyl, amino, mono- or di(lower alkyl)amino, cyclic amino optionally substituted with lower alkyl or cyclic amino, halogen and phenyl), substituted or unsubstituted $C_{7-20}$ aralkyl, $COR^1$ (in which $R^1$ represents hydrogen, substituted or unsubstituted $C_{6-10}$ nonheterocyclic aryl, substituted or unsubstituted heterocyclic group selected from the group consisting essentially of pyridyl, pyrazinyl and pyrimidinyl (wherein the substituted aralkyl, the substituted aryl and substituted heterocyclic group are substituted with 1 to 3 moieties independently selected from the group consisting of substituted or unsubstituted lower alkyl, lower alkoxy, lower alkoxycarbonyl, amino, mono- or di(lower alkyl)amino, pyrrole and halogen), $OR^2$ (in which $R^2$ represents substituted or unsubstituted lower alkyl or aryl), $SR^2$, $NR^3R^4$ (in which $R^3$ and $R^4$ independently represent hydrogen, amino, or mono- or di(lower alkyl)amino, provided that $R^3$ and $R^4$ are not hydrogen at the same time),

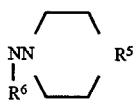

in which $R^5$ represents $NR^7$ (in which $R^7$ represents hydrogen or substituted or unsubstituted lower alkyl) or oxygen, and $R^6$ is the same meaning as $R^7$ defined above or

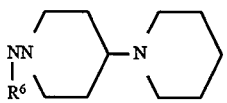

or $SO_2R^8$ (in which $R^8$ represents substituted or unsubstituted lower alkyl or substituted or unsubstituted aryl); and Y represents

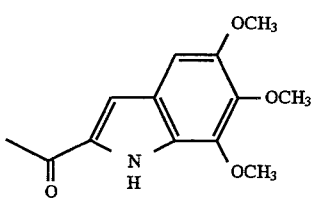

or

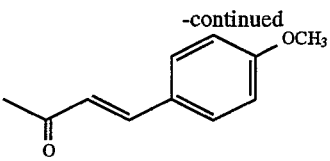

or pharmaceutically acceptable salts thereof.

2. A DC-89 derivative according to claim 1 represented by the formula

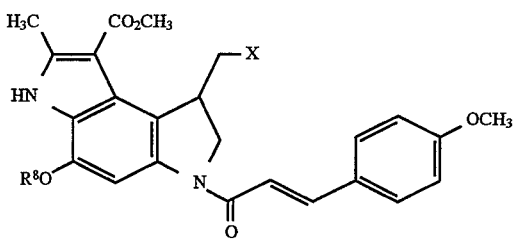

wherein X represents Cl or Br; and $R^a$ represents $COR^1$ (in which $R^1$ represents substituted or unsubstituted $C_{6-10}$ nonheterocyclic aryl, $NR^3R^4$ (in which $R^3$ and $R^4$ independently represent hydrogen, amino or mono- or di-(lower alkyl) amino, provided that $R^3$ and $R^4$ are not hydrogen atoms at the same time),

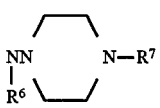

(in which $R^6$ and $R^7$ independently represent hydrogen or substituted or unsubstituted lower alkyl), or

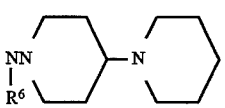

or pharmaceutically acceptable salts thereof.

3. A DC-89 derivative according to claim 1 represented by the formula

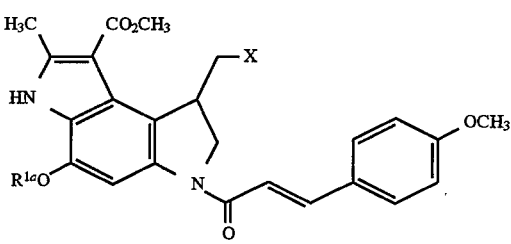

wherein X represents Cl or Br; and $R^{1a}$ represents

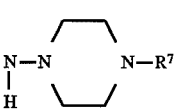

(in which $R^7$ represents hydrogen or substituted or unsubstituted lower alkyl), or

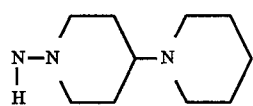
or pharmaceutically acceptable salts thereof.
* * * * *

UNITED STATES PATENT AND TRADEMARK OFFICE
CERTIFICATE OF CORRECTION

PATENT NO. : 5,641,780

DATED : June 24, 1997

INVENTOR(S) : NOBUYOSHI AMISHIRO, ET AL.          Page 1 of 2

It is certified that error appears in the above-identified patent and that said Letters Patent is hereby corrected as shown below:

COLUMN 5

Line 29, "changes" should read --change--.

COLUMN 7

Line 65, "desclosed" should read --disclosed--.

COLUMN 20

Line 43, "implantedat" should read --implanted at--.

COLUMN 28

Line 66 "methanol" correct line break.

COLUMN 30

Line 20, "1N-NMR" should read --'N-NMR--.

COLUMN 32

Line 9, "ehtanol" should read --ethanol--.

COLUMN 40

Line 49, "(cm);" should read --($cm^{-1}$);--.

COLUMN 45

Line 65, "$^J$=10.5," should read --J=10.5,--.

UNITED STATES PATENT AND TRADEMARK OFFICE
CERTIFICATE OF CORRECTION

PATENT NO. : 5,641,780

DATED : June 24, 1997

INVENTOR(S) : NOBUYOSHI AMISHIRO, ET AL.

It is certified that error appears in the above-identified patent and that said Letters Patent is hereby corrected as shown below:

COLUMN 46

Line 60, "1221." should read --1221, 1113.--.

COLUMN 48

Line 18, " $R^8O$ " should read -- $R^a O$ --.

Signed and Sealed this

Twenty-seventh Day of January, 1998

Attest:

BRUCE LEHMAN

Attesting Officer

Commissioner of Patents and Trademarks